(12) United States Patent
Bednarik et al.

(10) Patent No.: US 7,390,880 B2
(45) Date of Patent: Jun. 24, 2008

(54) SOLUBLE INTERLEUKIN-1 RECEPTOR ACCESSORY MOLECULE

(75) Inventors: Daniel P. Bednarik, Columbia, MD (US); Henrik S. Olsen, Gaithersburg, MD (US); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 337 days.

(21) Appl. No.: 11/066,006

(22) Filed: Feb. 25, 2005

(65) Prior Publication Data

US 2005/0171337 A1 Aug. 4, 2005

Related U.S. Application Data

(62) Division of application No. 08/917,710, filed on Aug. 26, 1997, now Pat. No. 6,974,682.

(60) Provisional application No. 60/024,581, filed on Aug. 26, 1996.

(51) Int. Cl.
C07K 14/00 (2006.01)
C07K 14/52 (2006.01)
(52) U.S. Cl. ........................ 530/350; 530/351
(58) Field of Classification Search ................ None
See application file for complete search history.

(56) References Cited

FOREIGN PATENT DOCUMENTS

WO WO-96/23067 8/1996

OTHER PUBLICATIONS

Jameson, et al., *Comp. Appl. Biosci..*, 4(1):181-186 (1988).
Federal Register, 66:1092-1099, esp. 1094 (2001).
Smith, et al., *Immunity*, 18:87-96 (2003).
Smith, et al., *Nature Biotechnology*, 15:1222-1223 (1997).
Brenner, *Trends in Genetics*, 15:132-133 (1999).
Skolnick, et al., *Trends in Biotech.*, 18:34-39 (2000).
Bork, P., *Genome Research*, 10:398-400 (2000).
Doerks, et al., *Trends in Genetics*, 14:248-250 (1998).
Bork, et al., *Trends in Genetics*, 12:425-427 (1996).
NCBI Entrez, GenBank Report with Reivision History, Accession No. T00021, McCombie, W.R., et al. (1992).
NCBI Entrez, GenBank Report with Revision History, Accession No. T08277, Adams, M.D., et al. (1993).
NCBI Entrez, GenBank Report with Revision History, Accession No. T11417, Takeda, J., et al. (1993).
NCBI Entrez, GenBank Report with Revision History, Accession No. T18224, Chakrabarti, D., et al. (1994).
NCBI Entrez, GenBank Report with Revision History, Accession No. T70598, Hillier, L., et al. (Mar. 1995).
NCBI Entrez, GenBank Report with Revision History, Accession No. T70863, Hillier, L., et al. (Mar. 1995).
NCBI Entrez, GenBank Report with Revision History, Accession No. T83863, Hillier, L., et al. (Mar. 1995).
NCBI Entrez, GenBank Report with Revision History, Accession No. T91161, Hillier, L., et al. (Mar. 1995).
NCBI Entrez, GenBank Report with Revision History, Accession No. R35902, Hillier, L., et al. (May 1995).
NCBI Entrez, GenBank Report with Revision History, Accession No. R35903, Hillier, L., et al. (May 1995).
NCBI Entrez, GenBank Report with Revision History, Accession No. R78680, Hillier, L., et al. (Jun. 1995).
NCBI Entrez, GenBank Report with Revision History, Accession No. T15223, Vandeloo, F.J., et al. (Jul. 1995).
NCBI Entrez, GenBank Report with Revision History, Accession No. D58283, Fujiwara, T., et al. (Aug. 1995).
NCBI Entrez, GenBank Report with Revision History, Accession No. D50979, Fujiwara, T., et al. (Sep. 1995).
NCBI Entrez, GenBank Report with Revision History, Accession No. D51799, Fujiwara, T., et al. (Sep. 1995).
NCBI Entrez, GenBank Report with Revision History, Accession No. H67866, Hillier, L., et al. (Oct. 1995).
NCBI Entrez, GenBank Report with Revision History, Accession No. H80533, Hillier, L., et al. (Nov. 1995).
NCBI Entrez, GenBank Report with Revision History, Accession No. H80590, Hillier, L., et al. (Nov. 1995).
NCBI Entrez, GenBank Report with Revision History, Accession No. H67866, Hillier, L., et al. (Dec. 1995).
NCBI Entrez, GenBank Report with Revision History, Accession No. D79417, Fujiwara, T., et al. (Feb. 1996).
NCBI Entrez, GenBank Report with Revision History, Accession No. D80043, Fujiwara T., et al. (Feb. 1996).
NCBI Entrez, GenBank Report with Revision History, Accession No. D80014, Fujiwara, T., et al. (Feb. 1996).
NCBI Entrez, GenBank Report with Revision History, Accession No. D80188, Fujiwara, T., et al. (Feb. 1996).
NCBI Entrez, GenBank Report with Revision History, Accession No. D80247, Fujiwara, T., et al. (Feb. 1996).
NCBI Entrez, GenBank Report with Revision History, Accession No. D80522, Fujiwara, T., et al. (Feb. 1996).
NCBI Entrez, GenBank Report with Revision History, Accession No. W85847, Hillier, L., et al. (Feb. 1997).

(Continued)

*Primary Examiner*—Elizabeth C. Kemmerer
*Assistant Examiner*—Sandra Wegert

(57) ABSTRACT

The present invention relates to a novel soluble IL-1 receptor accessory molecule (IL-1R AcM) protein which is a member of the Ig superfamily. In particular, isolated nucleic acid molecules are provided encoding the human IL-1R AcM protein. IL-1R AcM polypeptides are also provided as are vectors, host cells and recombinant methods for producing the same. Screening methods are futher provided for identifying agonist and antagonists of IL-1 signal transduction. The invention further relates to methods for treating physiologic and pathologic disease conditions with IL-1R AcM antagonists.

16 Claims, 5 Drawing Sheets

OTHER PUBLICATIONS

NCBI Entrez, GenBank Report with Revision History, Accession No. W85846, Hillier, L., et al. (Feb. 1997).
NCBI Entrez, GenBank Report with Revision History, Accession No. AA332636, Adams, M.D., et al. (Apr. 1997).
NCBI Entrez, GenBank Report with Revision History, Accession No. AA661179, Blaxter, M.L., et al. (Nov. 1997).
NCBI Entrez, GenBank Report with Revision History, Accession No. AA700260, Hillier, L., et al. (Dec. 1997).
NCBI Entrez, GenBank Report with Revision History, Accession No. AA753525, Nahm, B.H., et al. (1998).
NCBI Entrez, GenBank Report with Revision History, Accession No. AA752108, Nahm, B.H., et al. (1998).
NCBI Entrez, GenBank Report with Revision History, Accession No. AA751717, Nahm, B.H., et al. (1998).
NCBI Entrez, GenBank Report with Revision History, Accession No. AA751726, Nahm, B.H., et al. (1998).
NCBI Entrez, GenBank Report with Revision History, Accession No. AA753514, Nahm, B.H., et al. (1998).
NCBI Entrez, GenBank Report with Revision History, Accession No. AA754190, Nahm, B.H., et al. (1998).
NCBI Entrez, GenBank Report with Revision History, Accession No. AA754205, Nahm, B.H., et al. (1998).
NCBI Entrez, GenBank Report with Revision History, Accession No. F15046, Wintero, A.K., et al. (1998).
Adams, et al., "Rapid cDNA sequencing (expressed sequence tags) from a directionally cloned human infant brain cDNA library," *Nature Genetics*, 4:373-380 (1993).
Chizzonite, et al., "Two high-affinity interleukin 1 receptors represent separate gene products," *Proc. Natl. Acad. Sci. USA*, 86(20):8029-8033 (1989).
Colotta, et al., "Interleukin-1 type II receptor: a decoy target for IL-1 that is regulated by IL-4," *Science*, 261:472-475 (1993).
Curtis, et al., "T-cell interleukin 1 receptor cDNA expressed in Chinease hamster ovary cells regulates functional responses to interleukin 1," *Proc. Natl. Acad. Sci. USA*, 86:3045-3049 (1989).
Dinarello, et al., "The interleukin 1 receptor," *Immunol. Today*, 10(2):49-51 (1989).
Dinarello, C.A., "Interleukin-1 and Interleukin-1 antagonism," *Blood*, 77(8):1627-1652 (1991).
Dower, et al.,"Structure and function of murine and human IL-1 receptors," *Cellular and Molecular Mechanisms of Inflammation*, 1:137-172 (1990).
Greenfeder, et al., "Molecular cloning and characterization of a second subunit of the interleukin 1 receptor complex," *J. Biol. Chem.*, 270(23):13757-13765 (Jun. 1995).
Hibi, et al., "Molecular cloning and expression of an IL-6 signal transducer, gp130," *Cell*, 63:1149-1157 (1990).
Kitamura, et al., "Expression cloning of the human IL-3 receptor cDNA reveals a shared β subunit for the human IL-3 and GM-CSF receptors," *Cell*, 66:1165-1174 (1991).
Kupper, et al., "Interleukin 1 binds to specific receptors on human keratinocytes and induces granulocyte macrophage colony-stimulating factor mRNA and protein," *J. Clin. Invest.*, 82:1787-1792 (1988).

Liu, et al., "Rat homolog of mouse interleukin-1 receptor accessory protein: cloning, localization and modulation studies," *J. Neuroimmunology*, 66:41-48 (May 1996).
Mancilla, et al., "Glycosylation of the interleukin-1 receptor type I is required for optimal binding of interleukin-1." *Lymph. Cytok. Res.*, 11(4):197-205 (1992).
McMahan, et al., "A novel IL-1 receptor, cloned from B cells by mammalian expression, is expressed in many cell types," *EMBO, J.*, 10(10):2821-2832 (1991).
Minami, et al., "The IL-2 receptor complex: its structure, function, and target genes," *Annu. Rev. Immunol.*, 11:245-268 (1993).
Pimentel, E., "Interleukins and cytokines," in *Handbook of Growth Factors*: vol. III, CRC Press, Inc., Boca Raton, FL, pp. 35-53 (1994).
Sims, et al., "cDNA expression cloning of the IL-1 receptor, a member of the immunoglobulin superfamily," *Science*, 241:585-589 (1988).
Sims, et al., "Cloning the interleukin 1 receptor from human T cells," *Proc. Natl. Acad. Sci.* USA, 86:8946-8950 (1989).
Sims, et al., "Interleukin 1 signaling occurs exclusively via the type I receptor," *Proc. Natl. Acad. Sci.* USA, 90:6155-6159 (1993).
Solari, R., "Identification and distribution of two forms of the interleukin 1 receptor," *Cytokine*, 2(1):21-28 (1990).
Stylianou, et al., "Interleukin 1 induces NF-κB through its type I but not its type II receptor in lymphocytes," *J. Biol. Chem.*, 267(22):15836-15841 (1992).
Wesche, et al., "Co-expression of mRNA for type I and type II interleukin-1 receptors and the IL-1 receptor accessory protein correlates to IL-1 responsiveness," *FEBS Lett.*, 391:104-108 (Aug. 1996).
Database EST-STS on MASPAR search, WashU-Merck EST Project (St. Louis MO, USA) No. H80590, from Hillier, et al., "yu76e04.r1 Homo sapiens cDNA clone 239742 5" (Nov. 1995).
Database EST-STS on MASPAR search, WashU-Merck EST Project (St. Louis MO, USA) No. T70863, from Hillier, et al., "yd15f12.r1 Homo sapiens cDNA clone 108335 5" (Mar. 1995).
Genbank Report, Accession No. T85756, Hillier, et al., corresponding to database EST-STS, WashU-Merck EST Project (St. Louis MO, USA),"yd60e03.r1 Homo sapiens cDNA clone 112636 5" (Mar. 1995).
International Search Report for Application No. PCT/US96/13954, mailed Jan. 17, 1997.
Daniel, et al., *Virology*, 202:540-549 (1994).
Jensen et al., "IL-1 Signaling Cascade in Liver Cells and the Involvement of a Soluble Form of the IL-1 Receptor Accessory Protein," J. Immunol. 164:5277-5286 (2000).
Smeets et al., "Effectiveness of the Soluble Form of the Interleukin-1 Receptor Accessory Protein as an Inhibitor of Interleukin-1 in Collagen-Induced Arthritis," Arthritis & Rheumatism, 48(10):2949-2958 (Oct. 2003).
Smeets et al., "Soluble Interleukin-1 Receptor Accessory Protein Ameliorates Collagen-Induced Arthritis by a Different Mode of Action From That of Interleukin-1 Receptor Antagonist," Arthritis & Rheumatism, 52(7):2202-2211 (Jul. 2005).

```
  1 CGGTGGCGCCCGTTCTAGAACTAGTGGATCCCCCGGGATGCAGGAATTCGGCACGAGAAA    60
 61 GTGCGGCGGAAAGTAAGAGGCTCACTGGGGAAGACTGCCGGGATCCAGGTCTCCGGGGTC   120
121 CGCTTTGGCCAGAGGCGCGGAAGGAAGCAGTGCCCGGCGACACTGCACCCATCCCGGCTG   180
181 CTTTTGCTGCGCCCTCTCAGCTTCCCAAGAAAGGCATCGTCATGTGATCATCACCTAAGA   240
241 ACTAGAACATCAGCAGGCCCTTAGAAGCCTCACTCTTGCCCCTCCCTTTAATATCTCAAA   300
301 GGATGACACTTCTGTGGTGTGTAGTGAGTCTCTACTTTTATGGAATCCTGCAAAGTGATG   360
              M  T  L  L  W  C  V  V  S  L  Y  F  Y  G  I  L  Q  S  D  A
361 CCTCAGAACGCTGCGATGACTGGGGACTAGACACCATGAGGCAAATCCAAGTGTTTGAAG   420
     S  E  R  C  D  D  W  G  L  D  T  M  R  Q  I  Q  V  F  E  D
421 ATGAGCCAGCTCGCATCAAGTGCCCACTCTTTGAACACTTCTTGAAATTCAACTACAGCA   480
     E  P  A  R  I  K  C  P  L  F  E  H  F  L  K  F  N  Y  S  T
481 CAGCCCATTCAGCTGGCCTTACTCTGATCTGGTATTGGACTAAGCAGGACCGGGACCTTG   540
     A  H  S  A  G  L  T  L  I  W  Y  W  T  K  Q  D  R  D  L  E
541 AGGAGCCAATTAACTTCCGCCTCCCCGAGAACCGCATTAGTAAGGAGAAAGATGTGCTGT   600
     E  P  I  N  F  R  L  P  E  N  R  I  S  K  E  K  D  V  L  W
601 GGTTCCGGCCCACTCTCCTCAATGACACTGGCAACTATACCTGCATGTTAAGGAACACTA   660
     F  R  P  T  L  L  N  D  T  G  N  Y  T  C  M  L  R  N  T  T
661 CATATTGCAGCAAAGTTGCATTTCCCTTGGAAGTTGTTCAAAAAGACAGCTGTTTCAATT   720
     Y  C  S  K  V  A  F  P  L  E  V  V  Q  K  D  S  C  F  N  S
721 CCCCCATGAAACTCCCAGTGCATAAACTGTATATAGAATATGGCATTCAGAGGATCACTT   780
     P  M  K  L  P  V  H  K  L  Y  I  E  Y  G  I  Q  R  I  T  C
781 GTCCAAATGTAGATGGATATTTTCCTTCCAGTGTCAAACCGACTATCACTTGGTATATGG   840
     P  N  V  D  G  Y  F  P  S  S  V  K  P  T  I  T  W  Y  M  G
841 GCTGTTATAAAATACAGAATTTTAATAATGTAATACCCGAAGGTATGAACTTGAGTTTCC   900
     C  Y  K  I  Q  N  F  N  N  V  I  P  E  G  M  N  L  S  F  L
901 TCATTGCCTTAATTTCAAATAATGGAAATTACACATGTGTTGTTACATATCCAGAAAATG   960
     I  A  L  I  S  N  N  G  N  Y  T  C  V  V  T  Y  P  E  N  G
961 GACGTACGTTTCATCTCACCAGGACTCTGACTGTAAAGGTAGTAGGCTCTCCAAAAAATG  1020
     R  T  F  H  L  T  R  T  L  T  V  K  V  V  G  S  P  K  N  A
1021 CAGTGCCCCCTGTGATCCATTCACCTAATGATCATGTGGTCTATGAGAAAGAACCAGGAG 1080
     V  P  P  V  I  H  S  P  N  D  H  V  V  Y  E  K  E  P  G  E
1081 AGGAGCTACTCATTCCCTGTACGGTCTATTTTAGTTTTCTGATGGATTCTCGCAATGAGG 1140
     E  L  L  I  P  C  T  V  Y  F  S  F  L  M  D  S  R  N  E  V
1141 TTTGGTGGACCATTGATGGAAAAAAACCTGATGACATCACTATTGATGTCACCATTAACG 1200
     W  W  T  I  D  G  K  K  P  D  D  I  T  I  D  V  T  I  N  E
1201 AAAGTATAAGTCATAGTAGAACAGAAGATGAAACTAGAACTCAGATTTTGAGCATCAAGA 1260
     S  I  S  H  S  R  T  E  D  E  T  R  T  Q  I  L  S  I  K  K
1261 AAGTTACCTCTGAGGATCTCAAGCGCAGCTATGTCTGTCATGCTAGAAGTGCCAAAGGCG 1320
     V  T  S  E  D  L  K  R  S  Y  V  C  H  A  R  S  A  K  G  E
1321 AAGTTGCCAAAGCAGCCAAGGTGAAGCAGAAAGGTAATAGATGCGGTCAGTGATGAATCT 1380
     V  A  K  A  A  K  V  K  Q  K  G  N  R  C  G  Q  *
```

FIG.1A

1381 CTCAGCTCCAAATTAACATTGTGGTGAATAAGGACAAAAGGAGAGATTGAGAACAAGAGA 1440
1441 GCTCCAGCACCTAGCCTGACGGCATCTAACCCATAGTAATGAATCAAACTTAAATGAAAA 1500
1501 ATATGAAAGTTTTCATCTATGTAAGATACTCAAAATATTGTTTCTGATATTGTTAGTACC 1560
1561 GTAATGCCCAAATGTAGCTAAAAAAATCGACGTGAGTACAGTGAGACACAATTTTGTGTC 1620
1621 TGTACAATTATGAAAAATTAAAAACAAAGAAAATATTCAAAGCTACCAAAGATAGAAAAA 1680
1681 ACTGGTAGAGCCACATATTGTTGGTGAATTATTAAGACCCTTTTAAAAATCATTCATGGT 1740
1741 AGAGTTTAAGAGTCATAAAAAAGATTGCATCATCTGACCTAAGACTTTCGGAATTTTTCC 1800
1801 TGAACAAATAACAGAAAGGGAATTATATACCTTTTAATATTATTAGAAGCATTATCTGTA 1860
1861 GTTGTAAAACATTATTAATAGCAGCCATCCAATTGTATGCAACTAATTAAGGTATTGAAT 1920
1921 GTTTATTTTCCAAAAATGCATAATTATAATATTATTTTAAACACTATGTATCAATATTTA 1980
1981 AGCAGGTTTATAATATACCAGCAGCCACAATTGCTAAAATGAAAATCATTTAAATTATGA 2040
2041 TTTTAAATGGTATACACATGATTTCTATGTTGATAGTACTATATTATTCTACAATAAATG 2100
2101 GAAATTATAAAGCCTTCTTGTCAGAAGTGCTGCTCCTAAAAAAAAAAAAAAAAAA 2155

FIG.1B

| | | |
|---|---|---|
| Query: | 303 | MTLLWCVVSLYFYGILQSDASERCDDWGLDTMRQIQVFEDEPARIKCPLFEHFLKFNYST 482 |
| | | M LLW ++SL FYGILQS ASERCDDWGLDTMRQIQVFEDEPARIKCPLFEHFLK+NYST |
| Sbjct: | 1 | MGLLWYLMSLSFYGILQSHASERCDDWGLDTMRQIQVFEDEPARIKCPLFEHFLKYNYST 60 |
| | | |
| Query: | 483 | AHSAGLTLIWYWTKQDRDLEEPINFRLPENRISKEKDVLWFRPTLLNDTGNYTCMLRNTT 662 |
| | | AHS+GLTLIWYWT+QDRDLEEPINFRLPENRISKEKDVLWFRPTLLNDTGNYTCMLRNTT |
| Sbjct: | 61 | AHSSGLTLIWYWTRQDRDLEEPINFRLPENRISKEKDVLWFRPTLLNDTGNYTCMLRNTT 120 |
| | | |
| Query: | 663 | YCSKVAFPLEVVQKDSCFNSPMKLPVHKLYIEYGIQRITCPNVDGYFPSSVKPTITWYMG 842 |
| | | YCSKVAFPLEVVQKDSCFNS M+ PVHK+YIE+GI +ITCPNVDGYFPSSVKP ++TWY G |
| Sbjct: | 121 | YCSKVAFPLEVVQKDSCFNSAMRFPVHKMYIEHGIHKITCPNVDGYFPSSVKPSVTWYKG 180 |
| | | |
| Query: | 843 | CYKIQNFNNVIPEGMNLSFLIALISNNGNYTCVVTYPENGRTFHLTRTLTVKVVGSPKNA 1022 |
| | | C +I +F+NV+PEGMNLSF I L+SNNGNYTCVVTYPENGR FHLTRT+TVKVVGSPK+A |
| Sbjct: | 181 | CTEIVDFHNVLPEGMNLSFFIPLVSNNGNYTCVVTYPENGRLFHLTRTVTVKVVGSPKDA 240 |
| | | |
| Query: | 1023 | VPPVIHSPNDHVVYEKEPGEELLIPCTVYFSFLMDSRNEVWWTIDGKKPDDITIDVTINE 1202 |
| | | +PP I+SPND VVYEKEPGEEL+IPC VYFSF+MDS NEVWWTIDGKKPDD+T+D+TINE |
| Sbjct: | 241 | LPPQIYSPNDRVVYEKEPGEELVIPCKVYFSFIMDSHNEVWWTIDGKKPDDVTVDITINE 300 |
| | | |
| Query: | 1203 | SISHSRTEDETRTQILSIKKVTSEDLKRSYVCHARSAKGEVAKAAKVKQK 1352 |
| | | S+S+S TEDETRTQILSIKKVT EDL+R+YVCHAR+ KGE +AAKVKQK |
| Sbjct: | 301 | SVSYSSTEDETRTQILSIKKVTPEDLRRNYVCHARNTKGEAEQAAKVKQK 350 |

FIG.2A

```
   1 TCTATGAGAAAGAACCAGGAGAGGAGCTACTCATTCCCTGTACGGTCTAT   50
     ||||||||||||||||||||||||||||||||||||||||||||||||||
1060 TCTATGAGAAAGAACCAGGAGAGGAGCTACTCATTCCCTGTACGGTCTAT 1109

51 TTTAGTTTTCTGATGGATTCTCGCAATGAGGTTTGGTGGACCATTGATGG  100
     ||||||||||||||||||||||||||||||||||||||||||||||||||
1110 TTTAGTTTTCTGATGGATTCTCGCAATGAGGTTTGGTGGACCATTGATGG 1159

101 AAAAAAACCTGATGACATCACTATTGATGTCACCATTAACGAAAGTATAA  150
     ||||||||||||||||||||||||||||||||||||||||||||||||||
1160 AAAAAAACCTGATGACATCACTATTGATGTCACCATTAACGAAAGTATAA 1209

151 GTCATAGTAGAACAGAAGATGAAACAAGAACTCAGATTTTGAGCATCAAG  200
     ||||||||||||||||||||||||||||||||||||||||||||||||||
1210 GTCATAGTAGAACAGAAGATGAAACAAGAACTCAGATTTTGAGCATCAAG 1259

201 AAAGTTACCTCTGAGGATCTCAAGCGCANTANTGTCTGTCATGCTAGAAG  250
     |||||||||||||||||||||||||||| :  :|||||||||||||||||
1260 AAAGTTACCTCTGAGGATCTCAAGCGCAGCTATGTCTGTCATGCTAGAAG 1259

251 TGCCAAAGGCGAAGTTGCCAAAGCAGCCAAGGTGAAGCAGAAAG  294
     ||||||||||||||||||||||||||||||||||||||||||||
1310 TGCCAAAGGCGAAGTTGCCAAAGCAGCCAAGGTGAAGCAGAAAG 1353
```

SOLUBLE INTERLEUKIN-1 RECEPTOR ACCESSORY MOLECULE

CROSS REFRENCE TO RELATED APPLICATIONS

This application is a divisional of patent application Ser. No. 08/917,710, filed Aug. 26, 1997, now U.S. Pat. No. 6,974,682, which claims the benefit of the filing date of provisional application 60/024,581 filed on Aug. 26, 1996, each of which is herein incorporated by reference in its entirety.

BACKGROUND OF THE INVENTION

The present invention relates to a novel soluble Interleukin-1 receptor accessory molecule (IL-1R AcM). IL-1R AcM is a member of the Ig superfamily by analysis of its putative extracellular domain and bears limited homology throughout the protein to both Type I and Type II IL-1 receptors. More specifically, isolated nucleic acid molecules are provided encoding a human microvascular endothelial-derived soluble IL-1R AcM. The IL-1R AcM polypeptides are also provided. The present invention further relates to screening methods for putative agonists and antagonists of IL-1 signal transduction.

Interleukin 1 (IL-1) is a polypeptide cytokine with multiple diverse effects on immunological and inflammatory processes. While many of the roles of IL-1 in inflammation and the immune response have been well characterized, the molecular basis of these responses remains unclear (reviewed by Dinarello, *Blood*, 77: 1627-1652). IL-1 is produced by a diversity of cell types and elicits a wide variety of physiological effects in hematopoetic and nonhematopoetic cells. Thus, IL-1 has biological effects on hematopoietic cells, the digestive tract, bone, cartilage and connective tissue, vascular cells, the skin, the endocrine system, the gonads, and on neural tissue. In addition, IL-1 is produced by malignant cells. (Pimentel, *Handbook of Growth Factors: Volume III Hematopoietic Growth Factors and Cytokines*, pp. 35-53, CRC Press, Boca Raton, Fla. 1994).

The IL-1 family of proteins comprises three members: IL-1α and IL-1β (capable of inducing IL-1 biological responses) and IL-1ra (a pure receptor antagonist). These ligands bind to two distinct and separate receptors: the Type I and Type II IL-1 receptors (IL-1Rs). The 80-kD Type I IL-1R is found mainly on T cells and fibroblasts (Sims, J. E., et al., *Science* 241: 585-589 (1988); Chizzonite, R., et al., *Proc. Natl. Acad. Sci. USA* 86: 8029-8033 (1989); Sims, J. E., et al, *Proc. Natl. Acad, Sci. USA* 86:8946-8950 (1989)). The 68-kD Type II IL-1R is found predominantly on B cells and neutrophils (Chizzonite, R., et al., *Proc. Natl. Acad. Sci. USA* 86:8029-8033 (1989); Sims, J. E., et al., *Proc. Natl. Acad, Sci. USA* 86:8946-8950 (1989); McMahan, C. J., et al., *EMBO J.* 10:2821-2832 (1991)). Both receptor types contain a large cytoplasmic region, a single transmembrane domain, and three extracellular Ig-like domains, a structural organization that classifies them as members of the Ig superfamily. The Type I IL-1R has a cytoplasmic tail of approximately 200 amino acids, while the Type II IL-1R cytoplasmic tail is only 29 amino acids. The agonists IL-1α and IL-1β bind to the extracellular domains of both receptors, although with different affinities (reviewed in Dower et al., *Cellular and Molecular Mechanisms of Inflammation*, pp. 137-172, Academic Press, Orlando Fla.).

The relative importance of the Type I and Type II IL-1Rs in IL-1 signaling has been recently clarified. A critical role for the Type I IL-1R in IL-1-induced activation of NF-κB, IL-6, and IL-8 secretion, and cell adhesion molecule expression has been demonstrated by several groups (Stylianou, E., et al., *J. Biol. Chem.* 267:15836-15841 (1992); Colotta, F., et al., *Science* 261:472-475 (1993); Sims, J. E., et al., *Proc. Natl. Acad. Sci. USA* 90:6155-6159 (1993)). In contrast, the Type II IL-1R appears to be dispensable for IL-1 signaling and may act as a decoy receptor (Stylianou, E., et al., *J. Biol. Chem.* 267:15836-15841 (1992); Colotta, F., et al., *Science* 261:472-475 (1993); Sims, J. E., et al., *Proc. Natl. Acad. Sci. USA* 90:6155-6159 (1993)). While it appears clear that the Type I IL-1R is necessary for IL-1 signal transduction, it is uncertain if it is the only cell-surface molecule involved in IL-1 signaling.

It has been assumed that the functional Type I IL-1R is a single chain receptor (Curtis, B. M., et al., *Proc. Natl. Acad. Sci. USA*, 86:3045-3049 (1989)). However, affinity cross-linking of IL-1 to cells expressing natural IL-1 receptor has yielded complex patterns of cross-linked proteins (Dower, et al., *Cellular and Molecular Mechanisms of Inflammation*, pp. 137-172, Academic Press, Orlando Fla. (1990); Dinarello, et al., *Immunol. Today*, 10:49-51 (1989)). These cross-linking studies detect molecular mass complexes consistent with both the Type I and Type II IL-1Rs cross-linked to IL-1. In addition, in some studies, higher molecular mass complexes (>200 kD) are apparent (Kupper, T. S., et al., *J. Clin. Invest.* 82:1787-1792 (1988); Dinarello, C. A., et al., *Immunol. Today* 10:49-51 (1989); Solari, R., *Cytokine* 2:21-28 (1990); Mancilla, J., et al., *Lymph. Cytokine Res.* 11:197-205 (1992)). Some reports have interpreted these higher molecular mass complexes to be dimers of receptor-ligand complexes. Others have concluded that these high molecular mass complexes maybe indicative of a multi-subunit IL-1 receptor complex.

Only two IL-1R accessory proteins are have been identified. Studies initiated to identify components of a potential IL-1 receptor complex suggest that there is a cell-surface protein in close association with the IL-1R that may play a role in IL-1 receptor binding and signaling. A murine IL-1 receptor accessory protein (muIL-1 R AcP) has been cloned and expressed (Greenfeder et al. *J. Biol. Chem,* 270: 13757-13765 (1995)). This protein was present in brain, lung, spleen, and thymus tissues. A search of the GenBank data base with the muIL-1R AcP cDNA sequence revealed significant homology (82%) to a cDNA isolated from human infant brain (accession no. T08277) (Adams, M. D., et al., *Nature Genet.* 4:373-380 (1993)). No other significant homologies were found in GenBank. The reported sequence for this partial cDNA is 396 bp long and represents one of 1600 cDNAs that were sequenced from a library made to contain only expressed sequence tags. The regions to overlap with the muIL-1R AcP sequence is nucleotides 893-1286 of the muIL-R AcP, which include the transmembrane domain. Although Adams et al. (Adams, M. D., et al., *Nature Genet.* 4:373-380 (1993)) assigned no function to this partial cDNA, it is likely that it encodes a portion of a human homologue of muIIL-1R AcP. Using the muIIL-1R AcP cDNA has >95% homology to the partial sequence of Adams et al. and 90% homology to the muIL-1R AcP cDNA. This partial cDNA was isolated as an expressed gene in infant brain. This was consistent with Northern analysis results of Greenfeder et al. demonstrating that muIIL-1R AcP mRNA is constitutively expressed at high levels in mouse brain.

The discovery of IL-1R accessory molecule has a number of implications for IL-1 receptor biology. First, while muIL-1R AcM may not bind IL-1 directly, the accessory molecule forms a complex with the muType I IL-1R allowing IL-1β to bind with higher affinity than the muType I IL-1R alone (Greenfeder, et al. *J. Biol. Chem,* 270: 13757-13765 (1995)). Thus, the presence or absence of the accessory molecule in different cell lines determined whether the low or the higher affinity site was detected, suggesting that the low affinity site corresponds to the muType I IL-1R alone, while the higher affinity site represents a complex of the muType I IL-1R with the muIL-1R AcM. (Greenfeder, et al. *J. Biol. Chem,* 270: 13757-13765 (1995)). In this respect, the IL-1R AcM would be analogous to affinity conversion and signal transduction subunits such as gp 130 in the IL-6 system (Hibi, M., et al., *Cell* 63:1149-1157 (1990)), the common β chain of the IL-3, granulocyte/macrophage colony-stimulating factor, and IL-5 receptors (Kitamura, T., et al., *Cell* 66:1165-1174 (1991)), and the $\gamma_C$ subunit first identified as part of the IL-2 receptor (reviewed in Minami, et al., *Annu. Rev. Immunol.* 11: 245-267 (1993)).

Second, the possible existence of a multi-subunit IL-1 receptor complex contradicts a previous hypothesis that the Type I IL-1R is the entire functional receptor for IL-1 signaling (Dower, S. K. & Sims, J. E., *Cellular and Molecular Mechanisms of Inflammation,* Academic Press, Orlando, Fla. (1990), pp. 137-172; Curtis, B. M., et al., *Proc. Natl. Acad. Sci. USA,* 86:3045-3049 (1989)). This hypothesis was based on the observation that CHO cells expressing recombinant murine Type I IL-1R were more sensitive than control CHO cells to low concentrations of IL-1, and that the increase in sensitivity was proportional to the number of murine Type I IL-1Rs (Curtis, B. M., et al., *Proc. Natl. Acad. Sci. USA,* 86:3045-3049 (1989)). An alternative explanation for these results is that the endogenous hamster IL-1R, was able to form a functional receptor complex with the mu Type I IL-1R, thus enhancing IL-1 signaling in the transfected cells (Greenfeder, et al. *J. Biol. Chem,* 270: 13757-13765 (1995)).

Third, the discovery of the accessory protein provides an intriguing explanation for the antagonist activity of IL-1ra despite its high affinity binding to the Type I IL-1R. The inability of IL-1ra to interact with the muIL-1R AcP, the putative signal transducing subunit of the IL-1R complex, would result in the absence of a biological response.

BRIEF SUMMARY OF THE INVENTION

The present invention provides isolated nucleic acid molecules comprising a polynucleotide encoding the soluble IL-1R AcM polypeptide having the amino acid sequence as shown in FIG. 1A (SEQ ID NO:2) or the amino acid sequence encoded by the cDNA clone deposited as ATCC Deposit Number 97666 on Jul. 25, 1996. The nucleotide sequence determined by sequencing the deposited IL-1R AcM clone, which is shown in FIGS. 1A-B (SEQ ID NO:1), contains an open reading frame encoding a polypeptide of 356 amino acid residues, including an initiation codon at positions 303-305, with a leader sequence of about 17 amino acid residues, and a predicted molecular weight of about 42 kDa. The amino acid sequence of the mature IL-1R AcM protein is amino acid residues 18-356 shown in FIGS. 1A-B or 1-339 shown in SEQ ID NO:2.

The present invention also relates to recombinant vectors, which include the isolated nucleic acid molecules of the present invention, and to host cells containing the recombinant vectors, as well as to methods of making such vectors and host cells and for using them for production of soluble IL-1R AcM polypeptides or peptides by recombinant techniques.

The invention further provides an isolated soluble IL-1R AcM polypeptide having amino acid sequence encoded by a polynucleotide described herein.

The soluble IL-1R AcM may not bind IL-1 directly, however, the accessory molecule forms a complex with the Type I IL-1R that binds IL-1β with higher affinity than the Type I IL-1R alone. Thus, the presence or absence of the accessory molecule in different cell lines determines whether the low or the higher affinity site is detected suggesting that the low affinity site corresponds to the Type I IL-1R alone, while the higher affinity site represents a complex of the Type I IL-1R with the IL-1R AcM. The present invention further provides a screening method for identifying IL-1 receptor agonists and antagonists, which involves: (a) providing a polypeptide comprising a Type I IL-1 receptor and a polypeptide comprising IL-1R AcM or IL-1R AcM fragment, wherein IL-1R and IL-1R AcM or IL-1R and the IL-1R AcM fragment form a complex; (b) providing a candidate compound; (c) providing a polypeptide comprising IL-1 or a functional Il-1 fragment; and (d) determining the binding affinity of said complex for IL-1 whereby an increased binding affinity of said complex for IL-1 in the presence of said compound is indicative that said compound is an agonist for IL-1 signal transduction and a decreased binding affinity of said complex for IL-1 in the presence of said compound is indicative that said compound is an antagonist of IL-1 signal transduction.

BRIEF DESCRIPTION OF THE FIGURES

FIGS. 1A-B shows the nucleotide [SEQ ID NO:1] and deduced amino acid [SEQ ID NO:2] sequences of soluble IL-1R AcM. The protein has a leader sequence of about 17 amino acid residues (underlined) and a deduced molecular weight of about 42 kDa. The predicted amino acid sequence of the mature soluble IL-1R AcM protein is also shown in FIG. 1A [SEQ ID NO:2].

FIGS. 2A and B shows the regions of similarity between the amino acid sequences of the soluble IL-1R AcM protein (HMEEJ22) and mouse interleukin 1 receptor accessory protein [SEQ ID NO:3] and between the amino acid sequences of the soluble IL-1R AcM protein (HMEEJ22) and the partial cDNA isolated from human infant brain (Adams, M. D., et al., Nature Genet. 4:373-380 (1993)) [SEQ ID NO:4].

DETAILED DESCRIPTION OF THE INVENTION

Figure 3:
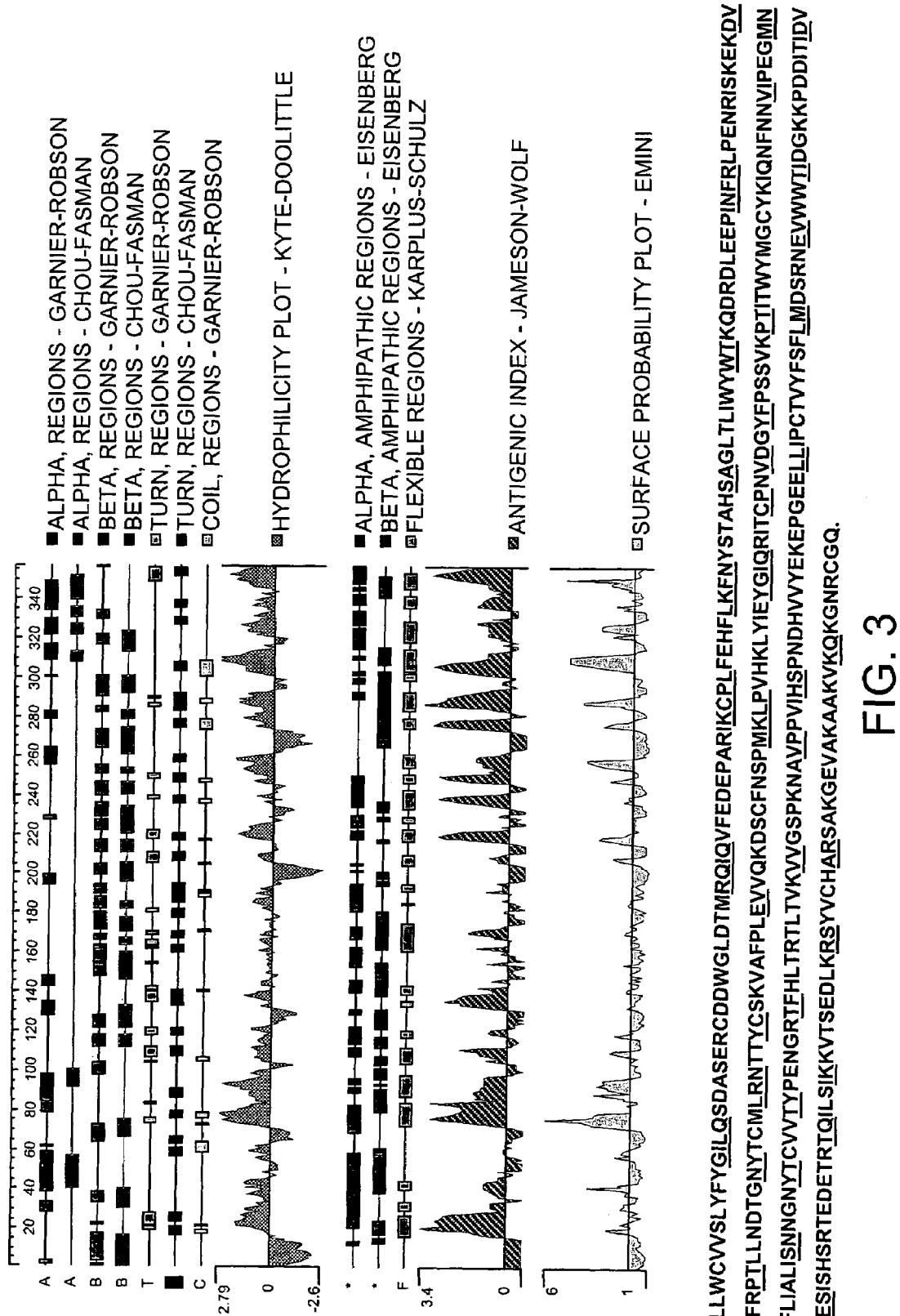
FIG. 3 shows an analysis of the IL-1R AcM amino acid sequence. Alpha, beta, turn and coil regions; hydrophilicity and hydrophobicity; amphipathic regions; flexible regions; antigenic index and surface probability are shown. The amino acid sequence of the IL-1R AcM protein is shown with the amino acids that border each peak from the "Antigenic Index—Jameson-Wolf" plot displayed as underlined characters.

The present invention provides isolated nucleic acid molecules comprising a polynucleotide encoding soluble IL-1R AcM polypeptide, having the amino acid sequence shown in FIG. 1A [SEQ ID NO:2], which was determined by sequencing a cloned cDNA. The soluble IL-1R AcM protein of the present invention shares sequence homology with mouse interleukin 1 receptor accessory protein (FIG. 2A) [SEQ ID NO:3]. The nucleotide sequence shown in FIGS. 1A-B [SEQ ID NO:1] was obtained by sequencing the HMEEJ22 clone, which was deposited on Jul. 25, 1996 at the American Type Culture Collection, Patent Depository, 10801 University Boulevard, Manassas, Va. 20110-2209, and given accession number 97666. The deposited clone is inserted in the pBluescript SK(−) plasmid (Stratagene, La Jolla, Calif.).

Accordingly, in one embodiment of the present invention, isolated nucleic acid molecules are provided which encode the soluble IL-1R AcM protein. The IL-1R AcM is a novel member of the Ig superfamily.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-B, a nucleic acid molecule of the present invention encoding a soluble IL-1R AcM polypeptide may be obtained using standard cloning and screening procedures, such as those for cloning cDNAs using mRNA as starting material. Illustrative of the invention, the nucleic acid molecule described in FIGS. 1A-B [SEQ ID NO:1] was discovered in a cDNA library derived from human microvascular endothelial cells. The determined nucleotide sequence of the soluble IL-1R AcM cDNA of FIGS. 1A-B [SEQ ID NO:1] contains an open reading frame encoding a protein of 356 amino acid residues, with an initiation codon at positions 303-306 of the nucleotide sequence in FIGS. 1A-B [SEQ ID NO:1], a predicted leader sequence of about 17 amino acid residues, and a deduced molecular weight of about 42 kDa. The amino acid sequence of the predicted mature soluble IL-1R AcM is amino acid residue 18 to residue 356 shown in FIG. 1A or amino acids 1-339 shown in SEQ ID NO:2. The soluble IL-1R AcM protein shown in FIG. 1A [SEQ ID NO:2] is about 94% similar and 85% identical to mouse interleukin 1 accessory protein (FIG. 2A). In addition, the nucleotides 1060 to 1353 of soluble IL-1R AcM protein shown in FIG. 1A [SEQ ID NO:2] is about 99% similar and 98% identical to the first 294 nucleotides partial cDNA isolated from human infant brain by Adams, M. D., et al., *Nature Genet.* 4:373-380 (1993) [SEQ ID NO:4] (FIG. 2B). The partial cDNA isolated by Adams was 396 nucleotides in length.

The present invention also provides the mature form(s) of the soluble IL-1R AcM protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature soluble IL-1R AcM polypeptides having the amino acid sequence encoded by the cDNA clone identified as ATCC Deposit No. 97666 and as shown in SEQ ID NO:2. By the mature soluble IL-1R AcM protein having the amino acid sequence encoded by the cDNA clone contained in the host identified as ATCC Deposit 97666 is meant the mature form(s) of the soluble IL-1R AcM protein produced by expression in a mammalian cell (e.g., COS cells, as described below) of the complete open reading frame encoded by the human DNA sequence of the clone contained in the vector. As indicated below, the mature soluble IL-1R AcM having the amino acid sequence encoded by the cDNA clone contained in ATCC Deposit No. 97666 may or may not differ from the predicted "mature" soluble IL-1R AcM protein shown in SEQ ID NO:2 (amino acids from about 1 to about 339) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete soluble IL-1R AcM polypeptides of the present invention were analyzed by a computer program ("PSORT") (K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acids −1 and 1 in SEQ ID NO:2. Thereafter, the complete amino acid sequences were further analyzed by visual inspection, applying a simple form of the (−1,−3) rule of von Heinje. von Heinje, supra. Thus, the leader sequence for the soluble IL-1R AcM protein is predicted to consist of amino acid residues from about −17 to about −1 in SEQ ID NO:2, while the mature soluble IL-1R AcM protein is predicted to consist of residues from about 1 to about 339.

As one of ordinary skill would appreciate, due to the possibilities of sequencing errors discussed above, as well as the variability of cleavage sites for leaders in different known proteins, the actual soluble IL-1R AcM polypeptide encoded by the deposited cDNA comprises about 356 amino acids, but may be anywhere in the range of 345-370 amino acids; and the actual leader sequence of this protein is about 17 amino acids, but may be anywhere in the range of about 10 to about 20 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 303-306 of the nucleotide sequence shown in FIGS. 1A-B [SEQ ID NO:1]; DNA molecules comprising the coding sequence for the mature soluble IL-1R AcM protein shown in FIG. 1A (last 339 amino acids) [SEQ ID NO:2]; and DNA molecules which comprise a sequence substantially different from those described above but which, due to the degeneracy of the genetic code, still encode the soluble IL-1R AcM protein. Of course, the genetic code is well known in the art. Thus, it would be routine for one skilled in the art to generate the degenerate variants described above.

In addition, the invention provides nucleic acid molecules having nucleotide sequences related to extensive portions of SEQ ID NO:1 which have been determined from the following related cDNA clones: HE8MI45R (SEQ ID NO:5), HWEBD79F (SEQ ID NO:6), HSJBY21R (SEQ ID NO:7), HCE4Z93R (SEQ ID NO:8), HTEBZ03RA (SEQ ID NO:9).

Sequences of public ESTs that relate to a portion of SEQ ID NO:1 have the following GenBank Accession Numbers: T70598 (SEQ ID NO:10), W85847 (SEQ ID NO:11), T83863 (SEQ ID NO:12), T08277 (SEQ ID NO:13), T70863 (SEQ ID NO:14), H80590 (SEQ ID NO:15), H80533 (SEQ ID NO:16), R35902 (SEQ ID NO:17), T91161 (SEQ ID NO:18), D79417 (SEQ ID NO:19), R35903 (SEQ ID NO:20), R78680 (SEQ ID NO:21) and W85846 (SEQ ID NO:22).

In another aspect, the invention provides isolated nucleic acid molecules encoding the soluble IL-1R AcM polypeptide having an amino acid sequence encoded by the cDNA clone contained in the plasmid deposited as ATCC Deposit No. 97666 on Jul. 25, 1996. In a further embodiment, nucleic acid molecules are provided encoding the mature soluble IL-1R AcM polypeptide or the full-length soluble IL-1R AcM polypeptide lacking the N-terminal methionine. The invention also provides an isolated nucleic acid molecule will encode the mature polypeptide encoded by the above-described deposited cDNA clone. The invention further provides an isolated nucleic acid molecule having the nucleotide sequence shown in FIGS. 1A-B [SEQ ID NO:1] or the nucleotide sequence of the soluble IL-1R AcM cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the soluble IL-1R AcM gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1500 or 2100 nt in length are also useful according to the present invention as are fragments corresponding to most, if not all, of the nucleotide sequence of the deposited cDNA or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit 97666. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in SEQ ID NO:1). Of course, a polynucleotide which hybridizes only to a poly A sequence (such as the 3' terminal poly(A) tract of the soluble IL-1R AcM cDNA shown in SEQ ID NO:1), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Since a soluble IL-1R AcM cDNA clone has been deposited and its determined nucleotide sequence is provided in FIGS. 1A-B [SEQ ID NO:1], generating polynucleotides which hybridize to a portion of the soluble IL-1R AcM cDNA molecule would be routine to the skilled artisan. For example, restriction endonuclease cleavage or shearing by sonication of the soluble IL-1R AcM cDNA clone could easily be used to generate DNA portions of various sizes which are polynucleotides that hybridize to a portion of the soluble IL-1R AcM cDNA molecule. Alternatively, the hybridizing polynucleotides of the present invention could be generated synthetically according to known techniques. Of course, a polynucleotide which hybridizes only to a poly A sequence (such as the 3' terminal poly(A) tract of the soluble IL-1R AcM cDNA shown in FIG. 1B [SEQ ID NO:1]), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

Preferred nucleic acid fragments of the present invention include nucleic acid molecules encoding epitope-bearing portions of the soluble IL-1R AcM protein. In particular, isolated nucleic acid molecules are provided encoding polypeptides comprising the following amino acid residues in FIG. 1A (SEQ ID NO:2), which the present inventors have determined are antigenic regions of the soluble IL-1R AcM protein: In particular, such nucleic acid fragments of the present invention include nucleic acid molecules encoding: a polypeptide comprising amino acid residues from about 6 to about 15 in SEQ ID NO:2; a polypeptide comprising amino acid residues from about 57 to about 66 in SEQ ID NO:2; a polypeptide comprising amino acid residues from about 70 to about 79 in SEQ ID NO:2; a polypeptide comprising amino acid residues from about 106 to about 112 in SEQ ID NO:2; a polypeptide comprising amino acid residues from about 115 to about 124 in SEQ ID NO:2; a polypeptide comprising amino acid residues from about 129 to about 135 in SEQ ID NO:2; a polypeptide comprising amino acid residues from about 158 to about 172 in SEQ ID NO:2; a polypeptide comprising amino acid residues from about 180 to about 187 in SEQ ID NO:2; a polypeptide comprising amino acid residues from about 207 to about 215 in SEQ ID NO:2; a polypeptide comprising amino acid residues from about 231 to about 244 in SEQ ID NO:2; a polypeptide comprising amino acid residues from about 247 to about 255 in SEQ ID NO:2; a polypeptide comprising amino acid residues from about 268 to about 276 in SEQ ID NO:2; a polypeptide comprising amino acid residues from about 285 to about 295 in SEQ ID NO:2; a polypeptide comprising amino acid residues from about 303 to about 310 in SEQ ID NO:2; a polypeptide comprising amino acid residues from about 319 to about 330 in SEQ ID NO:2; and a polypeptide comprising amino acid residues from about 333 to about 339 in SEQ ID NO:2. Methods for generating such epitope-bearing portions of soluble IL-1R AcM are described in detail below.

As indicated, nucleic acid molecules of the present invention which encode a soluble IL-1R AcM polypeptide may include, but are not limited to those encoding the amino acid sequence of the mature polypeptide, by itself, the coding sequence for the mature polypeptide and additional sequences, such as those encoding the about 17 amino acid leader or secretory sequence, such as a pre-, or pro- or preproprotein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the soluble IL-1R AcM fused to Fc at the N- or C-terminus.

The present invention further relates to variants of the nucleic acid molecules of the present invention, which encode portions, analogs or derivatives of the soluble IL-1R AcM protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the soluble IL-1R AcM protein or portions thereof. Also especially preferred in this regard are conservative substitutions. Most highly preferred are nucleic acid molecules encoding the mature protein having the amino acid sequence shown in FIG. 1A [SEQ ID NO:2] or the mature soluble IL-1R AcM amino acid sequence encoded by the deposited cDNA clone.

Further embodiments of the invention include isolated nucleic acid molecules comprising a polynucleotide having a nucleotide sequence at least 90% identical, and more preferably at least 95%, 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 1 to about 339 in SEQ ID NO:2; (d) a nucleotide sequence encoding the polypeptide having the amino acid sequence encoded by the cDNA clone contained in ATCC Deposit No. 97666; (e) a nucleotide sequence encoding the mature soluble IL-1R AcM polypeptide having the amino acid sequence encoded by the cDNA clone contained in ATCC Deposit No. 97666; or (f) a nucleotide sequence complementary to any of the nucleotide sequences in (a), (b), (c), (d) or (e).

By a polynucleotide having a nucleotide sequence at least, for example, 95% "identical" to a reference nucleotide sequence encoding a soluble IL-1R AcM polypeptide is intended that the nucleotide sequence of the polynucleotide is identical to the reference sequence except that the polynucleotide sequence may include up to five point mutations per each 100 nucleotides of the reference nucleotide sequence encoding the soluble IL-1R AcM polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIGS. 1A-B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIGS. 1A-B [SEQ ID NO:1] or to the nucleic acid sequence of the deposited cDNA, irrespective of whether they encode a polypeptide having soluble IL-1R AcM activity. This is because even where a particular nucleic acid molecule does not encode a polypeptide having soluble IL-1R AcM activity, one of skill in the art would still know how to use the nucleic acid molecule, for instance, as a hybridization probe or a polymerase chain reaction (PCR) primer. Uses of the nucleic acid molecules of the present invention that do not encode a polypeptide having soluble IL-1R AcM activity include, inter alia, (1) isolating the soluble IL-1R AcM gene or allelic variants thereof in a cDNA library; (2) in situ hybridization (e.g., "FISH") to metaphase chromosomal spreads to provide precise chromosomal location of the soluble IL-1R AcM gene, as described in Verma et al., *Human Chromosomes: A Manual of Basic Techniques*, Pergamon Press, New York (1988); and (3) Northern Blot analysis for detecting soluble IL-1R AcM mRNA expression in specific tissues.

Preferred, however, are nucleic acid molecules having sequences at least 90%, 95%, 97%, 98% or 99% identical to the nucleic acid sequence shown in FIGS. 1A-B [SEQ ID NO:1] or to the nucleic acid sequence of the deposited cDNA which do, in fact, encode a polypeptide having soluble IL-1R AcM protein activity. By "a polypeptide having soluble IL-1R AcM activity" is intended polypeptides exhibiting activity similar, but not necessarily identical, to an activity of the soluble IL-1R AcM protein of the invention (either the full-length protein or, preferably, the mature protein), as measured in a particular biological assay. Assays of IL-1R AcM protein activity are well-known to those in the art. These assays can be used to measure IL-1R AcM protein activity of partially purified or purified native or recombinant protein. For example, an equilibrium and competitive binding studies using CHO stable cell lines (Greenfeder et al., *J. Biol. Chem.* 270: 13757-13765 (1995)) can be performed to detect IL-1R AcM activity.

For this assay, a CHO-IR/AcM cell line is established by simultaneous cotransfection of two expression vectors such that both IL-1R and IL-1R AcM or a candidate IL-1R AcM are expressed at about a 1:10 ratio of molecules/cell. In addition, control cell lines which express only IL-1R or IL-1R AcM are also established. To establish the stable cell lines, CHO-dhfr cells are maintained in DMEM with 10% fetal bovine serum, 25 mM HEPES, pH 7.0, 0.1 mML glutamine, 1×HT supplement (0.1 mM hypoxanthine, 0.016 mM thymidine) (Boehringer Mannheim), 50 µg/ml gentamicin, 1×penicillin/streptomycin/fungizone (JRH Biosciences). Cells are transfected with pSV2-dhfr (Subramani, et al. *Mol. Cell. Biol.* 1: 845-864 (1981)) either alone or in combination with expression vectors containing IL-1R, IL-1R AcM protein and a candidate IL-1R AcM protein by the $CaPO_4$ method following the manufacturer's directions (Stratagene). After three days, cells are transferred to medium lacking HT and allowed to grow an additional two weeks. Transfectants are then subjected to gene amplification by growth in increasing doses of methotrexate (0.1-1.0 µM). Clones are isolated by limiting dilution and screened by equilibrium binding with $^{125}$I-labeled IL-1, anti-IL-1R antibody or anti-IL-1R AcM antibody.

To characterize the number and affinities of IL-1β binding sites, each of the above generated cell lines are analyzed by equilibrium binding with $^{125}$I-labeled IL-1β. Equilibrium binding of $^{125}$I-labeled IL-1 to the cells can performed as described by Mizel, et al. *J. Immunol.* 138: 2906-2912 (1987). $^{125}$I labeling of IL-1β can be performed by methods well known to those skilled in the art, for example, as described by Chizzonite, et al. *J. Immunol.* 147:1548-1556 (1991).

The activity of the accessory protein, IL-1R AcM, can be examined in the binding of IL-1β to a CHO-IR/AcM cell line obtained above. It is desirable for this cell line to express an excess amount of IL-1R AcM protein relative to IL-1R. Cell lines bearing only IL-1R AcM protein do not bind IL-1β and cell lines bearing only IL-R will bind IL-1β with low affinity (i.e., approximately $K_D$ 1.0-3.3 nM). A CHO-IR/AcM cell line, bearing both the IL-1R and IL-1R AcM results in IL-1R having a higher affinity binding site (i.e., approximately $K_D$ 0.02-0.8 nM). Thus, one can monitor the presence of IL-1R AcM activity by testing whether the putative accessory protein interacts with the IL-1R so as to generate a high affinity IL-1β binding site. The IL-1R AcM protein of the present invention can serve as a reference for the assay for IL-1R AcM activity associated with the high affinity IL-1R binding state.

In addition to the above described assay, one can evaluate whether a candidate polypeptide has IL-1R AcM activity by performing simple binding kinetics can be measured to determine receptor affinity for the ligand (i.e., IL-1β). Binding kinetic analysis experiments are well known to those skilled in the art (Chizzonite et al., *Proc Natl. Acad. Sci.* 86:8029-8033 (1989); Mizel, et al., *J. Immunol.* 138:2906-2912 (1987)). One can monitor the presence of IL-1R AcM activity by testing whether the putative accessory protein interacts with the IL-1R so as to result in high affinity binding of IL-1 to the receptor. The IL-1R AcM protein of the present invention can serve as a reference for the assay for IL-1R AcM activity associated with the high affinity IL-1R binding state.

Thus, "a polypeptide having soluble IL-1R AcM protein activity" includes polypeptides that exhibit IL-1R AcM activity, in the above-described assay. Although the degree of activity need not be identical to that of the IL-1R AcM protein, preferably, "a polypeptide having IL-1R AcM protein activity" will exhibit substantially similar activity as compared to the IL-1R AcM protein (i.e., the candidate polypeptide will exhibit greater activity or not more than about tenfold less and, preferably, not more than about ten-fold less activity relative to the reference IL-1R AcM protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIGS. 1A-B [SEQ ID NO:1] will encode a polypeptide "having soluble IL-1R AcM protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having soluble IL-1R AcM protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that are suprisingly tolerant of amino acid substitutions.

Vectors and Host Cells

The present invention also relates to vectors which include the isolated DNA molecules of the present invention, host cells which are genetically engineered with the recombinant vectors, and the production of soluble IL-1R AcM polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pA2, pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize receptors. For example, EP-A-O 464 533 (Canadian counterpart 2045869) discloses fusion proteins comprising various portions of constant region of immunoglobin molecules together with another human protein or part thereof. In many cases, the Fc part in fusion protein is thoroughly advantageous for use in therapy and diagnosis and thus results, for example, in improved pharmacokinetic properties (EP-A 0232 262). On the other hand, for some uses it would be desirable to be able to delete the Fc pat after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, shIL5-receptor has been fused with Fc portions for the purpose of high-throughput screening assays to identify antagonists of hIL-5. See, D. Bennett et al., *Journal of Molecular Recognition*, Vol. 8 52-58 (1995) and K. Johanson et al., *The Journal of Biological Chemistry*, Vol. 270, No. 16, pp 9459-9471 (1995).

The soluble IL-1R AcM protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

IL-1R AcM Polypeptides and Fragments

The invention further provides an isolated soluble IL-1R AcM polypeptide having the amino acid sequence encoded by the deposited cDNA, or the amino acid sequence in FIG. 1A [SEQ ID NO:2], or a peptide or polypeptide comprising a portion of the above polypeptides. The terms "peptide" and "oligopeptide" are considered synonymous (as is commonly recognized) and each term can be used interchangeably as the context requires to indicate a chain of at least to amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the soluble IL-1R AcM polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the soluble IL-1R AcM polypeptide which show substantial soluble IL-1R AcM polypeptide activity or which include regions of soluble IL-1R AcM protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247:1306-1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the soluble IL-1R AcM protein. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to or interaction with cell surface receptors. Ostade et al., *Nature* 361:266-268 (1993) describes certain mutations resulting in selective binding of TNF-α to only one of the two known types of TNF receptors. Thus, the soluble IL-1R AcM of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given soluble IL-1R AcM polypeptide will not be more than 50, 40, 30, 25, 20, 15, 10, 5 or 3.

Amino acids in the soluble IL-1R AcM protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding or interaction can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the soluble IL-1R AcM polypeptide can be substantially purified by the one-step method described in Smith and Johnson, *Gene* 67:31-40 (1988).

The polypeptides of the present invention include the polypeptide encoded by the deposited cDNA including the leader, the mature polypeptide encoded by the deposited the cDNA minus the leader (i.e., the mature protein), a polypeptide comprising amino acids about −17 to about 339 in SEQ ID NO:2; a polypeptide comprising amino acids about −16 to about 339 in SEQ ID NO:2; a polypeptide comprising amino acids about 1 to about 339 in SEQ ID NO:2; as well as polypeptides which are at least 80% identical, more preferably at least 90% or 95% identical, still more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a soluble IL-1R AcM polypeptide is intended that the amino acid sequence of the polypeptide is identical to the reference sequence except that the polypeptide sequence may include up to five amino acid alterations per each 100 amino acids of the reference amino acid of the soluble IL-1R AcM polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1A [SEQ ID NO:2] or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting soluble IL-1R AcM protein expression as described below or as agonists and antagonists capable of enhancing or inhibiting soluble IL-1R AcM protein function. Further, such polypeptides can be used in the yeast two-hybrid system to "capture" soluble IL-1R AcM protein binding proteins which are also candidate agonist and antagonist according to the present invention. The yeast two hybrid system is described in Fields and Song, *Nature* 340:245-246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37: 767-778 (1984) at 777.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention.

Non-limiting examples of antigenic polypeptides or peptides that can be used to generate soluble IL-1R AcM-specific antibodies include the following: a polypeptide comprising amino acid residues from about 6 to about 15 in SEQ ID NO:2; a polypeptide comprising amino acid residues from about 57 to about 66 in SEQ ID NO:2; a polypeptide comprising amino acid residues from about 70 to about 79 in SEQ ID NO:2; a polypeptide comprising amino acid residues from about 106 to about 112 in SEQ ID NO:2; a polypeptide comprising amino acid residues from about 115 to about 124 in SEQ ID NO:2; a polypeptide comprising amino acid residues from about 129 to about 135 in SEQ ID NO:2; a polypeptide comprising amino acid residues from about 158 to about 172 in SEQ ID NO:2; a polypeptide comprising amino acid residues from about 180 to about 187 in SEQ ID NO:2; a polypeptide comprising amino acid residues from about 207 to about 215 in SEQ ID NO:2; a polypeptide comprising amino acid residues from about 231 to about 244 in SEQ ID NO:2; a polypeptide comprising amino acid residues from about 247 to about 255 in SEQ ID NO:2; a polypeptide comprising amino acid residues from about 268 to about 276 in SEQ ID NO:2; a polypeptide comprising amino acid residues from about 285 to about 295 in SEQ ID NO:2; a polypeptide comprising amino acid residues from about 303 to about 310 in SEQ ID NO:2; a polypeptide comprising amino acid residues from about 319 to about 330 in SEQ ID NO:2; and a polypeptide comprising amino acid residues from about 333 to about 339 in SEQ ID NO:2.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131-5135. This "Simultaneous Multiple Peptide Synthesis (SMPS)" process is further described in U.S. Pat. No. 4,631,211 to Houghten et al. (1986).

As one of skill in the art will appreciate, soluble IL-1R AcM polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric soluble IL-1R AcM protein or protein fragment alone (Fountoulakis et al., *J. Biochem* 270: 3958-3964 (1995)).

Screening Applications of Soluble IL-1R AcM

The present inventors believe that soluble IL-1R AcM is involved in IL-1 activity and that it forms a complex with the Type I IL-1R allowing IL-1β to bind with higher affinity than to the Type I IL-1R alone. Thus, the presence or absence of the accessory molecule in different cell lines may determine whether the low or the high affinity site in the Type I IL-1R is formed. The low affinity site corresponds to the Type I IL-1R alone, while the higher affinity site represents a complex of the Type I IL-1R with the IL-1R AcM. Given that IL-1 has many diverse effects on immunologic and inflammatory process and that IL-1 elicits a wide variety of effects in hematic and nonhematic cells, it would be of interest to identify agonist and antagonist for IL-1 activity. IL-1R AcM may be necessary for IL-1 signal transduction events and may to be required for the formation of a high affinity IL-1R binding state. Stable cell lines established by simultaneous cotransfection of two expression vectors such that both IL-1R and IL-1R AcM are expressed at a 1:10 ratio of molecules/cell and control cell lines which express only IL-1R or IL-1R AcM could be used in screening assays to identify potential agonists and antagonists for IL-1. Thus, the present invention further provides a screening method of identifying IL-1 receptor agonists, which involves: (a) providing a host cell containing recombinant genes which express a polypeptide comprising a Type I IL-1 receptor and a polypeptide comprising IL-1R AcM or a IL-1R AcM fragment, wherein IL-1R and IL-1R AcM or an IL-1R AcM fragment form a complex; (b) administering a candidate agonist to said cell; and (c) determining the binding affinity of said complex for said candidate agonist relative to the binding of said comples for IL-1.

To characterize candidate IL-1R agonist binding to IL-1R, each of the cell lines are analyzed by equilibrium binding with $^{125}$I-labeled IL-1β. Equilibrium binding of $^{125}$I-labeled IL-1β to the cells can performed as described by Mizel, et al. *J. Immunol.* 138: 2906-2912 (1987) and Greenfeder et al., *J. Biol. Chem.* 270:13757-13765 (1995). The activity of the candidate agonist, can be examined relative to the binding of IL-1β to a CHO-IR/AcM cell line (as described, supra). It is desirable for this cell line to express an excess amount of IL-1R AcM protein relative to IL-1R. Cell lines bearing only IL-1R AcM protein will not bind IL-1β and cell lines bearing only IL-R bind IL-1β with low affinity (i.e., on the order of $K_D$ 1.0-3.3 nM). A CHO-IR/AcM cell line, bearing both the IL-1R and IL-1R AcM results in the IL-1R having a higher affinity binding site (i.e., on the order of $K_D$ 0.02-0.8 nM). Thus, one can monitor the relative binding affinity of the candidate agonist relative to the IL-1β. The presence of the IL-1R AcM protein of the present invention in the cell line used for agonist screening ensures that the IL1-R is in a high affinity binding state.

In a further aspect, the invention provides a screening method of identifying an IL-1 signal transduction antagonist. The results of Greenfeder, et al. (*J. Biol. Chem,* 270: 13757-13765 (1995)) suggest that the antagonist IL-1ra prevents or disrupts formation of a complex between muIL-1R and muIL-1R AcP. Thus, the screening method for identifying other antagonist of signal transduction which involves: (a) providing a host cell containing recombinant genes which express a polypeptide comprising a Type I IL-1 receptor and a polypeptide comprising IL-1R AcM or an IL-1R AcM fragment, wherein IL-1R and IL-1R AcM or IL-1R and the IL-1R AcM fragment form a complex; (b) administering a candidate antagonist to said cell; and (c) determining the whether said candidate antagonist disrupts or prevents formation of a complex between IL-1R and IL-1R AcM or IL-1R and the IL-1R AcM fragment.

In this antagonist screening assay, one can measure the formation of complex between IL-1R and IL-1R AcM by immunoprecipitating labeled protein complexes cross-linked to IL-1β, IL-1ra or the candidate antagonist. Using an anti-Type I IL-1R mAb or an anti-IL-1R AcM mAb, a protein complex of >200 kDa range will be observed for the cross linking reaction when IL-1β is used as a ligand indicating formation of an IL-1 binding complex. In addition, these antibodies will immunoprecipitate labeled IL1β. However, when labeled IL-1ra or a candidate antagonist is used as ligand, the anti-IL-1R AcM mAb will not immunoprecipitate the labeled agonist. Rather, the anti-IL-1R AcM antibody will only precipitate an IL-1ra or a candidate antagonist complex in the 100-120 kDa range indicating that the IL-1R and IL-1R AcM have not formed a complex.

Alternative Screening Assay

The present invention further provides a screening method for identifying IL-1 receptor agonists and antagonists, which involves: (a) providing a polypeptide comprising a Type I IL-1 receptor and a polypeptide comprising IL-1R AcM or IL-1R AcM fragment, wherein IL-1R and IL-1R AcM or IL-1R and the IL-1R AcM fragment form a complex; (b) providing a candidate compound; (c) providing a polypeptide comprising IL-1 or a functional IL-1 fragment; and (d) determining the binding affinity of said complex for IL-1 whereby an increased binding affinity of said complex for IL-1 in the presence of said compound is indicative that said compound is an agonist for IL-1 signal transduction and a decreased binding affinity of said complex for IL-1 in the presence of said compound is indicative that said compound is an antagonist of IL-1 signal transduction.

Candidate Agonists and Antagonists

Candidate antagonists and agonist according to the present invention inclulde IL-1ra, polypeptides and antibodies that either enhance or inhibit formation of the IL-1R IL-1R AcM complex. For example, an antibody that inhibits the murine IL-1R-IL-1R accessory protein complex is described in Greenfeder, et al. *J. Biol. Chem,* 270: 13757-13765 (1995). In addition, antibodies directed against murine Type I IL-1 receptors which block IL-1 activity are described in Chizzonite et al. *Proc. Natl. Acad Sci USA* 86: 8029 (1989); Lewis et al. *Eur. J. Immunol.* 20:207 (1990); Dinarello, *Int. J. Clin. Lab. Res.* 24:61-79 (1994). In addition, a point mutation in IL-1ra converts IL-1ra from an antagonist to a partial agonist of IL-1 activity in Ju et al. *Proc. Natl. Acad. Sci USA* 88:2658-2662 (1991). Others have developed recombinant IL-1 mutants with altered activities (Dinarello *Blood* 77:1627-1652; Gehrke et al. *J. Biol. Chem.* 265:5922-5925 (1990)). Thus, methods are known in the art for developing candidate IL-1R agonists and antagonists for screening in the present invention.

Methods for determining agonist or antagonist activity are known in the art (Ju et al. *Proc. Natl. Acad. Sci USA* 88:2658-2662 (1991); Dinarello *Blood* 77:1627-1652; Gehrke et al. *J. Biol. Chem.* 265:5922-5925 (1990)). Methods for determining whether a candidate agonist or antagonist enhances or interferes with the formation of the IL-1 receptor complex between IL-1R and IL-1R AcM is disclosed in Greenfeder et al., *J. Biol. Chem.* 270:13757-13765 (1995).

Administration of the candidate agonist or antagonist can be exogenous or endogenous and the candidate agonist or antagonist can be obtained from natural or recombinant sources. In addition, the screening method further provides for host cells containing recombinant genes expressing IL-1R and IL-1R AcM, as described above.

By "a host cell containing recombinant genes" is intended host cells which one or more of the recombinant constructs described herein have been introduced or a progeny of such host cells.

In addition, the invention provides antibodies directed to this accessory molecule which inhibit the interaction of IL-1R with IL-1R AcM thereby modulating IL-1 response of the cells. These antibodies could be useful for immunoprecipitating cross-linked complexes for the antagonist screening assay as well as showing that the stable cell lines are in fact expressing the Type I IL-1R and IL-1R AcM proteins. Methods for obtaining these antibodies are set forth below.

Soluble IL-1R AcM protein-specific antibodies for use in the present invention can be raised against the intact soluble IL-1R AcM protein or an antigenic polypeptide portion thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody portions (such as, for example, Fab and F(ab')$_2$ portions) which are capable of specifically binding to soluble IL-1R AcM protein. Fab and F(ab')$_2$ portions lack the Fc portion of intact antibody, clear more rapidly from the circulation, and may have less non-specific tissue binding of an intact antibody (Wahl et al., *J. Nucl. Med.* 24:316-325 (1983)). Thus, these portions are preferred.

The antibodies of the present invention may be prepared by any of a variety of methods. For example, cells expressing the soluble IL-1R AcM protein or an antigenic portion thereof can be administered to an animal in order to induce the production of sera containing polyclonal antibodies. In a preferred method, a preparation of soluble IL-1R AcM protein is prepared and purified as described above to render it substantially free of natural contaminants. Such a preparation is then introduced into an animal in order to produce polyclonal antisera of greater specific activity.

In the most preferred method, the antibodies of the present invention are monoclonal antibodies (or soluble IL-1R AcM protein binding portions thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas,* Elsevier, N.Y., pp. 563-681 (1981)). In general, such procedures involve immunizing an animal (preferably a mouse) with a soluble IL-1R AcM protein antigen or, more preferably, with a soluble IL-1R AcM protein-expressing cell. Suitable cells can be recognized by their capacity to bind soluble IL-1R AcM protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding the soluble IL-1R AcM antigen.

Alternatively, additional antibodies capable of binding to the soluble IL-1R AcM protein antigen may be produced in a two-step procedure through the use of anti-idiotypic antibodies. Such a method makes use of the fact that antibodies are themselves antigens, and therefore it is possible to obtain an antibody which binds to a second antibody. In accordance with this method, soluble IL-1R AcM protein specific antibodies are used to immunize an animal, preferably a mouse.

The splenocytes of such an animal are then used to produce hybridoma cells, and the hybridoma cells are screened to identify clones which produce an antibody whose ability to bind to the soluble IL-1R AcM protein-specific antibody can be blocked by the soluble IL-1R AcM protein antigen. Such antibodies comprise anti-idiotypic antibodies to the soluble IL-1R AcM protein-specific antibody and can be used to immunize an animal to induce formation of further soluble IL-1R AcM protein-specific antibodies.

It will be appreciated that Fab and F(ab')$_2$ and other portions of the antibodies of the present invention may be used according to the methods disclosed herein. Such portions are typically produced by proteolytic cleavage, using enzymes such as papain (to produce Fab portions) or pepsin (to produce F(ab')$_2$ portions). Alternatively, soluble IL-1R AcM protein-binding portions can be produced through the application of recombinant DNA technology or through synthetic chemistry.

Where in vivo imaging is used to detect enhanced levels of soluble IL-1R AcM protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4: 214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the soluble IL-1R AcM protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to antibodies are provided by Kennedy et al. (*Clin. Chim. Acta* 70: 1-31 (1976)), and Schurs et al. (*Clin. Chim. Acta* 81: 1-40 (1977)). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a soluble IL-1R AcM protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian*

Inheritance In Man, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Therapeutic Uses of Soluble IL-1R AcM

IL-1 has an important role in modulating the proliferation, maturation, and functional activation of hematopoietic cells, including lymphoid and nonlymphoid cells. IL-1 may have an important function in the regulation liver metabolism and be responsible for some of the marked changes in hepatic protein synthesis that occur in the acute phase response to inflammation or tissue injury. IL-1 is also involved in the regulation of bone remodulation, may be involved in the pathogenesis of chronic inflammatory joint diseases, such as rheumatoid arthritis, osteoarthritis, and may also play a role in the mechanisms of articular cartilage destruction hat occurs in degradative arthropathies. Human IL-1 is capable of increasing collagen protein and mRNA levels in cultured normal human dermal fibroblasts, thus, IL-1 may have a role in the early stages of scleroderma and other fibrotic diseases. IL-1 is capable of inducing a proliferative response in fibroblasts. In addition, IL-1 may have important effects on vascular cells, including endothelial cells and vascular smooth muscle cells. IL-1 may be involved in the pathogenesis of certain skin diseases, including chronic diseases such as psoriasis and epithelial fungus infections. IL-1 may have important effects on the functions of the hypothalamus-pituitary axis and thyroid gland. IL-1 has an important role in the regulation of insulin secretion by P cells in the pancreatic islets of Langerhans. Finally, IL-1 has important effects on the gonads and may play a role in the physiology of neural tissues. (Reviewed in Pimentel, *Handbook of Growth Factors: Volume III Hematopoietic Growth Factors and Cytokines*, pp. 35-53, CRC Press, Boca Raton, Fla. 1994).

Antibody Therapy

In view of the wide range of roles that IL-1 plays in physiologic and pathologic processes, regulating the action of IL-1 by abrogating signal transduction from the IL-1 binding complex is expected to be useful for therapeutic purposes. For example, recombinant IL-1ra blocks the activity of exogenously administered IL-1 in a variety of animal models. When rabbits or baboons are injected with IL-1 they develope hypertension which is prevented by a prior injection of IL-1ra (Ohlsson et al. *Nature* 348: 550 (1990); Fischer et al. *Am. J. Physiol.* 261: R442 (1991)). In animal studies, IL-1R blockade significantly reduces the severity of diseases, including those associated with infections, inflammation and metabolic disturbances (Arend, W. P. *J. Clin. Invest* 88:1445 (1991); Dinarello et al. *Immunol. Today* 12: 404 (1991)). In Table 1 of Dinarello, *Int. J. Clin. Lab. Res.* 24:61-79 (1994) (which is incorporated herein by reference) different models are listed wherein a specific reduction in IL-1R activity has been employed to reduce the disease severity.

In addition, studies with human subjects have also demonstrated that blockade of IL-1R is effective where the severity of disease is high. For example, dramatic results have been seen in patients with septic shock. In clinical trials there was a statistically significant reduction in mortality. (Dinarello, *Int. J. Clin. Lab. Res.* 24:61-79 (1994)).

In another clinical trial, rheumatoid arthritis patients treated with IL-1ra, in addition to other non-steroidal anti-inflammatory drugs, had a significant reduction in the number and severity of painful and swollen joints. These results demonstrate an improvement in the clincal disease of these patients. (Dinarello, *Int. J. Clin. Lab. Res.* 24:61-79 (1994)).

Similarly, antibodies produced to the murine Type I IL-1R have been used to block IL-1 effects in vitro and in vivo. (Chizzonite et al. *Proc. Natl. Acad Sci USA* 86:8029 (1989); Lewis et al. *Eur. J. Immunol.* 20:207 (1990)). For example, in animal models of infection and inflammation, administration of anti-IL-1R antibodies have reduced disease severity (Dinarello, *Int. J. Clin. Lab. Res.* 24:61-79 (1994)). The advantage of the anti-IL-1R antibodies is that they block IL-1 effects for several hours to days, whereas IL-1ra blood levels need to be sustained at sufficiently high levels to block IL-1 effects (Dinarello, *Int. J. Clin. Lab. Res.* 24:61-79 (1994)).

Given that IL-1R AcM is involved in IL-1 signal transduction, antibodies directed against IL-1R AcM are expected to behave as agonists or antagonist of IL-1 activity. For example, an antibody directed against the murine IL-1R accessory protein blocked the binding of IL-1β to murine Type I IL-1R (Greenfeder et al. *J. Biol. Chem,* 270: 13757-13765 (1995)). Thus, antibodies directed against the IL-1R AcM of the present invention that abrogate IL-1 activity can be used therapuetically to reduce the severity of diseases associated with IL-1.

Thus, the present invention is further directed antibody-based therapies which involve administering an anti-IL-1R AcM antibody to a mammalian, preferably human, patient for treating one or more of above-described disorders. Methods for producing anti-IL-1R AcM polyclonal and monoclonal antibodies are described in detail above. Such antibodies can may be provided in pharmaceutically acceptable compositions as known in the art or as described herein.

A summary of the ways in which the antibodies of the present invention may be used therapeutically includes binding IL-1R AcM locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The pharmaceutical compositions of the present invention may be administered by any means that achieve their intended purpose. Amounts and regimens for the administration of antibodies, their fragments or derivatives can be determined readily by those with ordinary skill in the clinical art of treating colon cancer and related disease.

For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 μg/kg body weight to about 5000 mg/kg body weight. The preferred dosages comprise 0.1 to 500 mg/kg body wt.

In addition to the pharmacologically active compounds, the new pharmaceutical compositions may contain suitable pharmaceutically acceptable carriers comprising excipients and auxiliaries which facilitate processing of the active compounds into preparations which can be used pharmaceutically. Preferably, the preparations, contain from about 0.01 to 99 percent, preferably from about 20 to 75 percent of active compound(s), together with the excipient.

Similarly, preparations of an IL-1R AcM antibody or fragment of the present invention for parenteral administration, such as in detectably labeled form for imaging or in a free or conjugated form for therapy, include sterile aqueous or non-aqueous solutions, suspensions, and emulsions. Examples of non-aqueous solvents are propylene glycol, polyethylene glycol, vegetable oil such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed., Mack Publishing Co., Easton, Pa., 1980.

In particular, the antibodies, fragments and derivatives of the present invention are useful for treating a subject having or developing IL-1R AcM related disorders as described herein. Such treatment comprises parenterally administering a single or multiple doses of the antibody, fragment or derivative, or a conjugate thereof.

The antibodies of this invention may be advantageously utilized in combination with other monoclonal or chimeric antibodies, or with lymphokines or hemopoietic growth factors, etc., which serve to increase the number or activity of effector cells which interact with the antibodies.

Since it appear to be necessary to block nearly all IL-1R's to block IL-1 activity, it is preferred to use high affinity and/or potent in vivo IL-1R AcM-inhibiting and/or neutralizing antibodies, fragments or regions thereof, for both IL-1R AcM immunoassays and therapy of IL-1 related disorders. Such antibodies, fragments, or regions, will preferably have an affinity for human IL-1R AcM, expressed as Ka, of at least $10^8$ $M^{-1}$, more preferably, at least $10^9$ $M^{-1}$, such as $5 \times 10^8$ $M^{-1}$, $8 \times 10^8$ $M^{-1}$, $2 \times 10^9$ $M^{-1}$, $4 \times 10^9$ $M^{-1}$, $6 \times 10^9$ $M^{-1}$, $8 \times 10^9$ $M^{-1}$.

Preferred for human therapeutic use are high affinity murine and murine/human or human/human chimeric antibodies, and fragments, regions and derivatives having potent in vivo IL-1-inhibiting and/or neutralizing activity, according to the present invention, e.g., that block IL-1-induced IL-6 secretion, and mitogenic activity, in vivo, in situ, and in vitro.

Having generally described the invention, the same will be more readily understood by reference to the following examples, which are provided by way of illustration and are not intended as limiting.

EXAMPLES

Example 1

Expression and Purification of IL-1R AcM in *E. coli*

The DNA sequence encoding the mature soluble IL-1R AcM protein in the deposited cDNA clone is amplified using PCR oligonucleotide primers specific to the amino acid carboxyl terminal sequence of the soluble IL-1R AcM protein and to vector sequences 3' to the gene. Additional nucleotides containing restriction sites BamHI and SalI to facilitate cloning are added to the 5' and 3' sequences, respectively.

The 5' oligonucleotide primer has the sequence 5' GGATCCATGACACTTCTGTGGTGTG 3' (SEQ ID NO:23) containing the underlined BamHI restriction site, followed by 16 nucleotides complementary to bp 1834-1853 of the antisense strand of the IL-1R AcM protein coding sequence set out in FIG. 1 (SEQ ID NO:1).

The 3' primer has the sequence 5' GTCGACTCACTGACCGCATCT 3' (SEQ ID NO:24) containing the underlined SalI restriction site, followed by 15 nucleotides complementary to bp 1056-1071 of the sense strand of the IL-1R AcM protein coding sequence set out in FIGS. 1A-B (SEQ ID NO:1), and a stop codon.

The restrictions sites are convenient to restriction enzyme sites in the bacterial expression vector pQE-9, which is used for bacterial expression in these examples. (Qiagen, Chatsworth, Calif., 91311).

The amplified IL-1R AcM protein DNA and the vector pQE-9 are both digested with BamHI and SalI and the digested DNAs are subsequently ligated together. Insertion of the IL-1R AcM protein DNA into the pQE-9 restricted vector places the IL-1R AcM protein coding region downstream of and operably linked to the vector's promoter and in-frame with an initiating AUG appropriately positioned for translation of IL-1R AcM protein.

The ligation mixture is transformed into competent *E. coli* cells using standard procedures. Such procedures are described, for example, in Sambrook et al., *Molecular Cloning: A Laboratory Manual*, 2nd Ed., Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), is used in carrying out the illustrative example described here. This strain, which is only one of many that are suitable for expressing IL-1R AcM protein, is available commercially from Qiagen.

Transformants are identified by their ability to grow on LB plates in the presence of ampicillin. Plasmid DNA is isolated from resistant colonies and the identity of the cloned DNA is confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") are then added to a final concentration of 1 mM to induce transcription from lac repressor sensitive promoters, by inactivating the lacI repressor. Cells subsequently are incubated further for 3 to 4 hours. Cells are then harvested by centrifugation and disrupted, by standard methods. Inclusion bodies are purified from the disrupted cells using routine collection techniques, and protein are solubilized from the inclusion bodies into 8M urea. The 8M urea solution containing the solubilized protein is passed over a PD-10 column in 2×phosphate buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 micrograms per mL.

Analysis of the preparation by standard methods of polyacrylamide gel electrophoresis reveals that the preparation contains about 95% monomer IL-1R AcM protein having the expected molecular weight of approximately 42 kDa.

Example 2

Cloning and Expression in Mammalian Cells

Most of the vectors used for the transient expression of the IL-R AcM protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC 12MI (ATCC 67109). Mammalian host cells that could be used include, human Hela, 283, H9 and Jurkart cells, mouse NIH3T3 and C127 cells, Cos 1, Cos 7 and CVi, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438-447 (March, 1985)) plus a fragment of the CMV-enhancer (Boshart et al., *Cell* 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 2(a)

Cloning and Expression in COS Cells

The expression plasmid, pIL-1R AcM HA, is made by cloning a cDNA encoding IL-R AcM into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the IL-1R AcM protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection of the recombinant protein with an antibody that recognizes the HA epitope.

The plasmid construction strategy is as follows. The IL-1RAcM cDNA of the deposited clone is amplified using primers that contain convenient restriction sites, much as described above regarding the construction of expression vectors for expression of IL-R AcM in *E. coli*. To facilitate detection, purification and characterization of the expressed IL-1R AcM, one of the primers contains a hemagglutinin tag ("HA tag") as described above.

Suitable primers include the following, which are used in this example. The 5' primer, containing the underlined BamHI site, an AUG start codon and 5 codons of the 5' coding region has the following sequence:

5'
    GG ATCC ATCCGCCATCATGACACTTCTGTGGTGTG 3' (SEQ ID NO:25).

The 3' primer, containing the underlined XbaI site, a stop codon, 9 codons thereafter forming the hemagglutinin HA tag, and 12 bp of 3' coding sequence (at the 3' end) has the following sequence:

```
                                              (SEQ ID NO:26)
5'TCTAGAAAAGCGTAGTCTGGGACGTCGTATGGGTACTGA

CCGCATCT 3'.
```

The PCR amplified DNA fragment and the vector, pcDNAI/Amp, are digested with BamHI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the IL-1R AcM-encoding fragment.

For expression of recombinant IL-1R AcM, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of IL-1R AcM by the vector.

Expression of the IL-1R AcM HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 2(b)

Cloning and Expression in CHO Cells

The vector pC1 is used for the expression of IL-1R AcM protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357-1370, Hamlin, J. L. and Ma, C. 1990, Biochem. et Biophys. Acta, 1097:107-143, Page, M. J. and Sydenham, M. A. 1991, Biotechnology Vol. 9:64-68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438-4470) plus a fragment isolated from the enhancer of the immediate early gene of human cytomegalovirus (CMV) (Boshart et al., Cell 41:521-530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding IL-1R AcM, ATCC 97666, is amplified using PCR oligonucleotide primers corresponding to the 5' and 3' sequences of the gene: The 5' primer has the sequence 5'GACT GGATCCGCCATCATGACACTTCTGTGGTGTG 3' (SEQ ID NO:27) containing the underlined BamHI restriction enzyme site followed by 19 bases of the sequence of IL-1R AcM of FIGS. 1A-B (SEQ ID NO:1). Inserted into an expression vector, as described below, the 5' end of the amplified fragment encoding human IL-1R AcM provides an efficient signal peptide. An efficient signal for initiation of translation in eukaryotic cells, as described by Kozak, M., J. Mol. Biol. 196:947-950 (1987) is appropriately located in the vector portion of the construct.

The 3' primer has the sequence 5' GAATTCCTCACTGACCGCATCT 3' (SEQ ID NO:28) containing the EcoRI restriction followed by nucleotides complementary to the last 15 nucleotides of the IL-1R AcM coding sequence set out in FIGS. 1A-B (SEQ ID NO:1), including the stop codon.

The amplified fragments are isolated from a 1% agarose gel as described above and then digested with the endonucleases BamHI and EcoRI and then purified again on a 1% agarose gel.

The isolated fragment and the dephosphorylated vector are then ligated with T4 DNA ligase. E. coli HB 101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10-14 days. After this period, single clones are trypsinized and then seeded in 6-well petri dishes using different concentrations of methotrexate (25 nM, 50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones grow at a concentration of 100 μM.

The expression of the desired gene product is analyzed by Western blot analysis and SDS-PAGE or by reverse phase HPLC analysis.

Example 3

Cloning and Expression of the Soluble IL-1R AcM Protein in a Baculovirus Expression System The cDNA sequence encoding the soluble IL-1R AcM protein in the deposited clone was amplified using PCR oligonucleotide primers corresponding to the 5' and 3' sequences of the gene: The 5' primer has the sequence 5' GACT GGATCCGCCATCATGACACTTCTGTGGTGTG 3' (SEQ ID NO:29) containing the underlined BamHI restriction enzyme site followed by 19 bases (bp 1834-1853) complementary to the antisense strand of the soluble IL-1R AcM protein coding sequence of FIGS. 1A-B (SEQ ID NO:1). Inserted into an expression vector, as described below, the 5' end of the amplified fragment encoding soluble IL-1R AcM protein receptor provides an efficient signal peptide. An efficient signal for initiation of translation in eukaryotic cells, as described by Kozak, M., *J. Mol. Biol.* 196:947-950 (1987), may be located, as appropriate, in the vector portion of the construct.

For the full length gene, the 3' primer has the full length sequence 5' GAC TGGTACCCA TAG AAA TCA TGT GTA TAC C 3' (SEQ ID NO:30), containing the underlined Asp718 restriction followed by 25 nucleotides complementary to bp 2049-2070 of the sense strand of the soluble IL-1R AcM protein set out in FIGS. 1A-B [SEQ ID NO:1], and a stop codon.

The amplified fragment was isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein "F2".

The vector pA2 is used to express the soluble IL-1R AcM protein in the baculovirus expression system, using standard methods, such as those described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cellmediated homologous recombination with wild-type viral DNA to generate viable virus that express the cloned polynucleotide.

Many other baculovirus vectors could be used in place of pA2, such as pAc373, pVL941 and pAcIMl provided, as those of skill readily will appreciate, that construction provides appropriately located signals for transcription, translation, trafficking and the like, such as an in frame AUG and a signal peptide, as required. Such vectors are described, for example, in Luckow et al., *Virology* 170:31-39 (1989). Suitable vectors will be readily apparent to the skilled artisan.

The plasmid was digested with the restriction enzymes BamHI and Asp718 and then was dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 were ligated together with T4 DNA ligase. *E. Coli* HB 101 cells were transformed with ligation mix and spread on culture plates. Bacteria were identified that contain the plasmid with the human soluble IL-1R AcM protein gene by digesting DNA from individual colonies using BamHI and Asp718 and then analyzing the digestion product by gel electrophoresis. The sequence of the cloned fragment was confirmed by DNA sequencing. This plasmid is designated herein as pA2HG16302.

5 μg of plasmid pA2HG16302 was co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413-7417 (1987). 1 μg of BaculoGold™ virus DNA and 5 μg of the plasmid pA2HG16302 were mixed in a sterile well of a microliter plate containing 50 μl of serum free Grace's medium (Life Technologies Inc., Gaithersburg, Md.). Afterwards, 10 μl Lipofectin plus 90 μl Grace's medium were added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was rocked back and forth to mix the newly added solution. The plate is then incubated for 5 hours at 27° C. After 5 hours the transfection solution was removed from the plate and 1 ml of Grace's insect medium supplemented with 10% fetal calf serum is added. The plate is put back into an incubator and cultivation is continued at 27° C. for four days.

After four days the supernatant was collected and a plaque assay was performed, as described by Summers and Smith, supra. An agarose gel with "Blue Gal" (Life Technologies Inc., Gaithersburg, Md.) is used to allow easy identification and isolation of gal-expressing clones, which produce blue-stained plaques. A detailed description of a "plaque assay" of this type can also be found in the user's guide for insect cell culture and baculovirology distributed by Life Technologies Inc., Gaithersburg, Md., at pages 9-10.

Four days after serial dilution, the virus was added to the cells. After appropriate incubation, blue stained plaques are picked with the tip of an Eppendorf pipette. The agar containing the recombinant viruses was then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they were stored at 4° C. A clone containing properly inserted soluble IL-1R AcM cDNA was identified by DNA analysis including restriction mapping and sequencing. This clone is designated herein as pA2HG16302.

Sf9 cells are grown in Grace's medium supplemented with 10% heat-inactivated FBS. The cells are infected with the recombinant baculovirus A2HG16302 at a multiplicity of infection ("MOI") of about 2 (about 1 to about 3). Six hours later the medium is removed and is replaced with SF900 II medium minus methionine and cysteine (available from Life Technologies Inc., Gaithersburg, Md.). 42 hours later, 5 μCi of $^{35}$S methionine and 5 MCi $^{35}$S cysteine (available from Amersham) are added. The cells are further incubated for 16 hours and then they are harvested by centrifugation, lysed and the labeled proteins are visualized by SDS-PAGE and autoradiography.

Example 4

Tissue Distribution of Soluble IL-1R AcM Protein Expression

Northern blot analysis is carried out to examine the levels of expression of the gene encoding the IL-1R AcM protein in human tissues, using methods described by, among others, Sambrook et al., cited above. A cDNA probe containing the entire nucleotide sequence of the IL-1R AcM protein of the present invention (SEQ ID NO:1) is labeled with $^{32}$P using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe is then used to examine various human tissues for the expression of the gene encoding the IL-1R AcM protein.

Multiple Tissue Northern (MTN) blots containing various human tissues (H) or human immune system tissues (IM) are obtained from Clontech and were examined with labelled probe using ExpressHyb™ Hybridization Solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of each document cited in this application is hereby incorporated herein by reference.

---

The invention claimed is:

1. An isolated polypeptide selected from the group consisting of:
   (a) a polypeptide comprising amino acids −17 to 339 of SEQ ID NO:2;
   (b) a polypeptide comprising amino acids 1 to 339 of sequence of SEQ ID NO:2;
   (c) a polypeptide comprising the full-length IL-1R AcM polypeptide encoded by the cDNA clone contained in ATCC Deposit No. 97666; and
   (d) a polypeptide comprising the mature IL-1R AcM polypeptide encoded by the cDNA clone contained in ATCC Deposit No. 97666.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. The isolated polypeptide of claim 1, wherein said polypeptide is glycosylated.

7. The isolated polypeptide of claim 1, wherein said polypeptide is fused to a heterologous polypeptide.

8. An isolated polypeptide produced by a method comprising:
   (a) expressing the polypeptide of claim 1 by a cell; and
   (b) recovering said polypeptide.

9. An isolated polypeptide selected from the group consisting of:
   (a) a polypeptide consisting of amino acids −17 to 339 of SEQ ID NO:2;
   (b) a polypeptide consisting of amino acids 1 to 339 of sequence of SEQ ID NO:2;
   (c) a polypeptide consisting of the full-length IL-1R AcM polypeptide encoded by the cDNA clone contained in ATCC Deposit No. 97666; and
   (d) a polypeptide consisting of the mature IL-1R AcM polypeptide encoded by the cDNA clone contained in ATCC Deposit No. 97666.

10. The isolated polypeptide of claim 9, wherein said polypeptide is (a).

11. The isolated polypeptide of claim 9, wherein said polypeptide is (b).

12. The isolated polypeptide of claim 9, wherein said polypeptide is (c).

13. The isolated polypeptide of claim 9, wherein said polypeptide is (d).

14. The isolated polypeptide of claim 9, wherein said polypeptide is glycosylated.

15. The isolated polypeptide of claim 9, wherein said polypeptide is fused to a heterologous polypeptide.

16. An isolated polypeptide produced by a method comprising:
   (a) expressing the polypeptide of claim 9 by a cell; and
   (b) recovering said polypeptide.

* * * * *

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 2155 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 303..1370

(ix) FEATURE:
      (A) NAME/KEY: sig_peptide
      (B) LOCATION: 303..353

(ix) FEATURE:
      (A) NAME/KEY: mat_peptide
      (B) LOCATION: 354..1370

(xi) SEQUENCE DESCRIPTION: SEQ ID NO: 1:

```
CGGTGGCGCC CGTTCTAGAA CTAGTGGATC CCCCGGGATG CAGGAATTCG GCACGAGAAA      60

GTGCGGCGGA AAGTAAGAGG CTCACTGGGG AAGACTGCCG GGATCCAGGT CTCCGGGGTC     120

CGCTTTGGCC AGAGGCGCGG AAGGAAGCAG TGCCCGGCGA CACTGCACCC ATCCCGGCTG     180

CTTTTGCTGC GCCCTCTCAG CTTCCCAAGA AAGGCATCGT CATGTGATCA TCACCTAAGA     240

ACTAGAACAT CAGCAGGCCC TTAGAAGCCT CACTCTTGCC CCTCCCTTTA ATATCTCAAA     300

GG ATG ACA CTT CTG TGG TGT GTA GTG AGT CTC TAC TTT TAT GGA ATC        347
   Met Thr Leu Leu Trp Cys Val Val Ser Leu Tyr Phe Tyr Gly Ile
   -17         -15                 -10                 -5

CTG CAA AGT GAT GCC TCA GAA CGC TGC GAT GAC TGG GGA CTA GAC ACC       395
Leu Gln Ser Asp Ala Ser Glu Arg Cys Asp Asp Trp Gly Leu Asp Thr
            1               5                   10

ATG AGG CAA ATC CAA GTG TTT GAA GAT GAG CCA GCT CGC ATC AAG TGC       443
Met Arg Gln Ile Gln Val Phe Glu Asp Glu Pro Ala Arg Ile Lys Cys
15                  20                  25                  30

CCA CTC TTT GAA CAC TTC TTG AAA TTC AAC TAC AGC ACA GCC CAT TCA       491
```

```
                    Pro Leu Phe Glu His Phe Leu Lys Phe Asn Tyr Ser Thr Ala His Ser
                                    35                  40                  45

GCT GGC CTT ACT CTG ATC TGG TAT TGG ACT AAG CAG GAC CGG GAC CTT               539
Ala Gly Leu Thr Leu Ile Trp Tyr Trp Thr Lys Gln Asp Arg Asp Leu
                50                  55                  60

GAG GAG CCA ATT AAC TTC CGC CTC CCC GAG AAC CGC ATT AGT AAG GAG               587
Glu Glu Pro Ile Asn Phe Arg Leu Pro Glu Asn Arg Ile Ser Lys Glu
            65                  70                  75

AAA GAT GTG CTG TGG TTC CGG CCC ACT CTC CTC AAT GAC ACT GGC AAC               635
Lys Asp Val Leu Trp Phe Arg Pro Thr Leu Leu Asn Asp Thr Gly Asn
        80                  85                  90

TAT ACC TGC ATG TTA AGG AAC ACT ACA TAT TGC AGC AAA GTT GCA TTT               683
Tyr Thr Cys Met Leu Arg Asn Thr Thr Tyr Cys Ser Lys Val Ala Phe
 95                 100                 105                 110

CCC TTG GAA GTT GTT CAA AAA GAC AGC TGT TTC AAT TCC CCC ATG AAA               731
Pro Leu Glu Val Val Gln Lys Asp Ser Cys Phe Asn Ser Pro Met Lys
                115                 120                 125

CTC CCA GTG CAT AAA CTG TAT ATA GAA TAT GGC ATT CAG AGG ATC ACT               779
Leu Pro Val His Lys Leu Tyr Ile Glu Tyr Gly Ile Gln Arg Ile Thr
            130                 135                 140

TGT CCA AAT GTA GAT GGA TAT TTT CCT TCC AGT GTC AAA CCG ACT ATC               827
Cys Pro Asn Val Asp Gly Tyr Phe Pro Ser Ser Val Lys Pro Thr Ile
        145                 150                 155

ACT TGG TAT ATG GGC TGT TAT AAA ATA CAG AAT TTT AAT AAT GTA ATA               875
Thr Trp Tyr Met Gly Cys Tyr Lys Ile Gln Asn Phe Asn Asn Val Ile
    160                 165                 170

CCC GAA GGT ATG AAC TTG AGT TTC CTC ATT GCC TTA ATT TCA AAT AAT               923
Pro Glu Gly Met Asn Leu Ser Phe Leu Ile Ala Leu Ile Ser Asn Asn
175                 180                 185                 190

GGA AAT TAC ACA TGT GTT GTT ACA TAT CCA GAA AAT GGA CGT ACG TTT               971
Gly Asn Tyr Thr Cys Val Val Thr Tyr Pro Glu Asn Gly Arg Thr Phe
                195                 200                 205

CAT CTC ACC AGG ACT CTG ACT GTA AAG GTA GTA GGC TCT CCA AAA AAT              1019
His Leu Thr Arg Thr Leu Thr Val Lys Val Val Gly Ser Pro Lys Asn
            210                 215                 220

GCA GTG CCC CCT GTG ATC CAT TCA CCT AAT GAT CAT GTG GTC TAT GAG              1067
Ala Val Pro Pro Val Ile His Ser Pro Asn Asp His Val Val Tyr Glu
        225                 230                 235

AAA GAA CCA GGA GAG GAG CTA CTC ATT CCC TGT ACG GTC TAT TTT AGT              1115
Lys Glu Pro Gly Glu Glu Leu Leu Ile Pro Cys Thr Val Tyr Phe Ser
    240                 245                 250

TTT CTG ATG GAT TCT CGC AAT GAG GTT TGG TGG ACC ATT GAT GGA AAA              1163
Phe Leu Met Asp Ser Arg Asn Glu Val Trp Trp Thr Ile Asp Gly Lys
255                 260                 265                 270

AAA CCT GAT GAC ATC ACT ATT GAT GTC ACC ATT AAC GAA AGT ATA AGT              1211
Lys Pro Asp Asp Ile Thr Ile Asp Val Thr Ile Asn Glu Ser Ile Ser
                275                 280                 285

CAT AGT AGA ACA GAA GAT GAA ACT AGA ACT CAG ATT TTG AGC ATC AAG              1259
His Ser Arg Thr Glu Asp Glu Thr Arg Thr Gln Ile Leu Ser Ile Lys
            290                 295                 300

AAA GTT ACC TCT GAG GAT CTC AAG CGC AGC TAT GTC TGT CAT GCT AGA              1307
Lys Val Thr Ser Glu Asp Leu Lys Arg Ser Tyr Val Cys His Ala Arg
        305                 310                 315

AGT GCC AAA GGC GAA GTT GCC AAA GCA GCC AAG GTG AAG CAG AAA GGT              1355
Ser Ala Lys Gly Glu Val Ala Lys Ala Ala Lys Val Lys Gln Lys Gly
    320                 325                 330

AAT AGA TGC GGT CAG TGATGAATCT CTCAGCTCCA AATTAACATT GTGGTGAATA              1410
Asn Arg Cys Gly Gln
335
```

```
AGGACAAAAG GAGAGATTGA GAACAAGAGA GCTCCAGCAC CTAGCCTGAC GGCATCTAAC    1470

CCATAGTAAT GAATCAAACT TAAATGAAAA ATATGAAAGT TTTCATCTAT GTAAGATACT    1530

CAAAATATTG TTTCTGATAT TGTTAGTACC GTAATGCCCA AATGTAGCTA AAAAAATCGA    1590

CGTGAGTACA GTGAGACACA ATTTTGTGTC TGTACAATTA TGAAAATTA AAACAAAGA     1650

AAATATTCAA AGCTACCAAA GATAGAAAAA ACTGGTAGAG CCACATATTG TTGGTGAATT    1710

ATTAAGACCC TTTTAAAAAT CATTCATGGT AGAGTTTAAG AGTCATAAAA AAGATTGCAT    1770

CATCTGACCT AAGACTTTCG GAATTTTTCC TGAACAAATA ACAGAAAGGG AATTATATAC    1830

CTTTTAATAT TATTAGAAGC ATTATCTGTA GTTGTAAAAC ATTATTAATA GCAGCCATCC    1890

AATTGTATGC AACTAATTAA GGTATTGAAT GTTTATTTTC CAAAAATGCA TAATTATAAT    1950

ATTATTTTAA ACACTATGTA TCAATATTTA AGCAGGTTTA TAATATACCA GCAGCCACAA    2010

TTGCTAAAAT GAAATCATT TAAATTATGA TTTTAAATGG TATACACATG ATTTCTATGT     2070

TGATAGTACT ATATTATTCT ACAATAAATG GAATTATAA AGCCTTCTTG TCAGAAGTGC     2130

TGCTCCTAAA AAAAAAAAAA AAAAA                                         2155

(2) INFORMATION FOR SEQ ID NO: 2:

(i) SEQUENCE CHARACTERISTICS:
        (A) LENGTH: 356 amino acids
        (B) TYPE: amino acid
        (D) TOPOLOGY: linear (ii) MOLECULE TYPE: protein (xi) SEQUENCE DESCRIPTION: SEQ ID NO: 2:

Met Thr Leu Leu Trp Cys Val Val Ser Leu Tyr Phe Tyr Gly Ile Leu
-17     -15                 -10                 -5

Gln Ser Asp Ala Ser Glu Arg Cys Asp Asp Trp Gly Leu Asp Thr Met
  1           5                  10                  15

Arg Gln Ile Gln Val Phe Glu Asp Glu Pro Ala Arg Ile Lys Cys Pro
                20                  25                  30

Leu Phe Glu His Phe Leu Lys Phe Asn Tyr Ser Thr Ala His Ser Ala
            35                  40                  45

Gly Leu Thr Leu Ile Trp Tyr Trp Thr Lys Gln Asp Arg Asp Leu Glu
        50                  55                  60

Glu Pro Ile Asn Phe Arg Leu Pro Glu Asn Arg Ile Ser Lys Glu Lys
    65                  70                  75

Asp Val Leu Trp Phe Arg Pro Thr Leu Leu Asn Asp Thr Gly Asn Tyr
 80                  85                  90                  95

Thr Cys Met Leu Arg Asn Thr Thr Tyr Cys Ser Lys Val Ala Phe Pro
                100                 105                 110

Leu Glu Val Val Gln Lys Asp Ser Cys Phe Asn Ser Pro Met Lys Leu
            115                 120                 125

Pro Val His Lys Leu Tyr Ile Glu Tyr Gly Ile Gln Arg Ile Thr Cys
        130                 135                 140

Pro Asn Val Asp Gly Tyr Phe Pro Ser Ser Val Lys Pro Thr Ile Thr
    145                 150                 155

Trp Tyr Met Gly Cys Tyr Lys Ile Gln Asn Phe Asn Asn Val Ile Pro
160                 165                 170                 175

Glu Gly Met Asn Leu Ser Phe Leu Ile Ala Leu Ile Ser Asn Asn Gly
                180                 185                 190

Asn Tyr Thr Cys Val Val Thr Tyr Pro Glu Asn Gly Arg Thr Phe His
            195                 200                 205
```

```
Leu Thr Arg Thr Leu Thr Val Lys Val Val Gly Ser Pro Lys Asn Ala
        210                 215                 220

Val Pro Pro Val Ile His Ser Pro Asn Asp His Val Val Tyr Glu Lys
225                 230                 235

Glu Pro Gly Glu Glu Leu Leu Ile Pro Cys Thr Val Tyr Phe Ser Phe
240                 245                 250                 255

Leu Met Asp Ser Arg Asn Glu Val Trp Trp Thr Ile Asp Gly Lys Lys
                260                 265                 270

Pro Asp Asp Ile Thr Ile Asp Val Thr Ile Asn Glu Ser Ile Ser His
                275                 280                 285

Ser Arg Thr Glu Asp Glu Thr Arg Thr Gln Ile Leu Ser Ile Lys Lys
        290                 295                 300

Val Thr Ser Glu Asp Leu Lys Arg Ser Tyr Val Cys His Ala Arg Ser
        305                 310                 315

Ala Lys Gly Glu Val Ala Lys Ala Ala Lys Val Lys Gln Lys Gly Asn
320                 325                 330                 335

Arg Cys Gly Gln (2) INFORMATION FOR SEQ ID NO: 3:

(i) SEQUENCE CHARACTERISTICS:
        (A) LENGTH: 350 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO: 3:

Met Gly Leu Leu Trp Tyr Leu Met Ser Leu Ser Phe Tyr Gly Ile Leu
1               5                   10                  15

Gln Ser His Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
            35                  40                  45

Leu Phe Glu His Phe Leu Lys Tyr Asn Tyr Ser Thr Ala His Ser Ser
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Ala Met Arg Phe
            130                 135                 140

Pro Val His Lys Met Tyr Ile Glu His Gly Ile His Lys Ile Thr Cys
145                 150                 155                 160

Pro Asn Val Asp Gly Tyr Phe Pro Ser Ser Val Lys Pro Ser Val Thr
                165                 170                 175

Trp Tyr Lys Gly Cys Thr Glu Ile Val Asp Phe His Asn Val Leu Pro
            180                 185                 190

Glu Gly Met Asn Leu Ser Phe Phe Ile Pro Leu Val Ser Asn Asn Gly
            195                 200                 205
```

```
Asn Tyr Thr Cys Val Val Thr Tyr Pro Glu Asn Gly Arg Leu Phe His
    210                 215                 220
Leu Thr Arg Thr Val Thr Val Lys Val Val Gly Ser Pro Lys Asp Ala
225                 230                 235                 240
Leu Pro Pro Gln Ile Tyr Ser Pro Asn Asp Arg Val Val Tyr Glu Lys
                245                 250                 255
Glu Pro Gly Glu Glu Leu Val Ile Pro Cys Lys Val Tyr Phe Ser Phe
            260                 265                 270
Ile Met Asp Ser His Asn Glu Val Trp Trp Thr Ile Asp Gly Lys Lys
        275                 280                 285
Pro Asp Asp Val Thr Val Asp Ile Thr Ile Asn Glu Ser Val Ser Tyr
    290                 295                 300
Ser Ser Thr Glu Asp Glu Thr Arg Thr Gln Ile Leu Ser Ile Lys Lys
305                 310                 315                 320
Val Thr Pro Glu Asp Leu Arg Arg Asn Tyr Val Cys His Ala Arg Asn
                325                 330                 335
Thr Lys Gly Glu Ala Glu Gln Ala Ala Lys Val Lys Gln Lys
            340                 345                 350

(2) INFORMATION FOR SEQ ID NO: 4:

(i) SEQUENCE CHARACTERISTICS:
        (A) LENGTH: 294 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO: 4:

TCTATGAGAA AGAACAAGGA GAGGAGCTAC TCATTCCCTG TACGGTCTAT TTTAGTTTTC      60

TGATGGATTC TCGCAATGAG GTTTGGTGGA CCATTGATGG AAAAAAACCT GATGACATCA    120

CTATTGATGT CACCATTAAC GAAAGTATAA GTCATAGTAG AACAGAAGAT GAAACAAGAA    180

CTCAGATTTT GAGCATCAAG AAAGTTACCT CTGAGGATCT CAAGCGCANT ANTGTCTGTC    240

ATGCTAGAAG TGCCAAAGGC GAAGTTGCCA AAGCAGCCAA GGTGAAGCAG AAAG          294

(2) INFORMATION FOR SEQ ID NO: 5:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

AGGAACCTCC AAACATATAG AAGTAAAGAC ACAGGGCTGT TATAAAATAC AGAATTTTAA      60

TAATGTAATA CCCGAAGGTA TGANCTTGAG TTTCCTCATT GCCTTAATTT CAAATAATGG    120

AAATTACACA TGTNTTGTTA CATATCCAGA AAATGGACGT ACGTTTCATC TCACCAGGAC    180

TCTGCTCTNT AAAGGTAGTA GGCTCTCCAA AAANTGCAGT GCCCCCTGTG ATCCATTCAC    240

CTAATGATCA TG                                                         252

(2) INFORMATION FOR SEQ ID NO: 6:

(i) SEQUENCE CHARACTERISTICS:
        (A) LENGTH: 425 base pairs
        (B) TYPE: nucleic acid
```

(C) STRANDEDNESS: single
        (D) TOPOLOGY: linear (ii) MOLECULE TYPE: cDNA (xi) SEQUENCE DESCRIPTION: SEQ ID NO: 6:

GAGACAGCGT CTTGCTCTGT CACCTGGGCT GGAGTGCAGT GGCGAGATCT CGGCTCACTG     60

CAACCTCTGC CTCCCAGGTT CAAGCAATTC TCCTGCCTCA CCCTCCTGAG TAGCTGGGAT    120

TACAGGTGTA TGCCACCATG CCGGCTAATT TTTGTATTTT CTAGTAGAGA CTAGGTTTCA    180

CCATGTTGGC CAGGCTGGTC TTGAACTATT TTTTTTTCTT TTTCTCGTGC CGAATTCCTG    240

CAGCCCGGGG GATCCACTAG TTCTAGAGCG GCCGCCACCG CGGTGGAGCT CCAGCTTTTG    300

TTCCCTTTAG TGAGGGNTAA TTTCGAGCTT GGCGTAATCA TGGTCATAGC TGTTTCCTGT    360

GTGAAATTGT TATCCGCTCA CAATTTCACA CAACATACGA GCCGGAAGCA TAAAGTGTAA    420

AGCCT                                                                425

(2) INFORMATION FOR SEQ ID NO: 7:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

TCACNNAAGG GACAAAAGCT GGAGCTCCAC CGCGGGCNGC NCGTTCTAGA ACTAGTGGAT     60

CCCCCGGGCT GCAGGAATTC                                                 80

(2) INFORMATION FOR SEQ ID NO: 8:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

GAACTAGTGG ATCCCCCGGG CTGCAGGAAT TCGNCACGAG ACCANCTCAC CTTTCCCCAC     60

ACTAGCTCAN GNACAGACAG ANTGGACTAA AAATAGTTGA                          100

(2) INFORMATION FOR SEQ ID NO: 9:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

GNCTAGAACT AGTGGATCCC CCGGGCTGCA GGAATTCGGC ACGAGGGGCT GCTCGAGCTG     60

CCAACAACGG AGCATTGCCC CCTGGACCTN AGCTGACATC GTGCGTAGNC TAGGCATGNG    120

TGGTTGTAGG GACTTACGTC TTTCTACCNT GANNCACGGT TATCACTGNC GANGTCCACC    180

CACCGGGGNT GNNCAACTTN CGGNGGAAGG TACTACNTAC TTTCAAACCC CCTAACTTGT    240

TCCTTTTTTG CAGGATCGAG TN                                             262

(2) INFORMATION FOR SEQ ID NO: 10:

(i) SEQUENCE CHARACTERISTICS:
        (A) LENGTH: 401 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
NTTAGTGTAC AGACACAAAA TTGTGTCTCA CTGTACTCAC GTCGATTTTT TTAGCTACAT        60

TTGGGCATTA CGGTACTAAC AATATCAGAA ACAATATTTT GAGTATCTTA CATAGATGAA       120

AACTTTCATA TTTTTCATTT AAGTTTGATT CATTACTATG GGTTAGATGC CGTCGGNTAG       180

GTGCTGGAGC TCTCTTGTTC TCAATCTCTC CTTTTGTCCT TATTCACCAC AATGTTAATT       240

TGGAGCTGAG AGATTCATCA CTGACCGCAT CTATTACCTT TCTGCTTCAC CTTGGCTGCT       300

TTGGCAACTT CGCCTTTGGA CCTTCTAGCA TGACAGACAT AGCTGCGCTT GAGATCCTCA       360

GAGGTAACTT TCTTGANGCT CAAAATCTGA GTTCTTGTTT C                          401
```

(2) INFORMATION FOR SEQ ID NO: 11:

(i) SEQUENCE CHARACTERISTICS:
        (A) LENGTH: 443 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
CATAATTGTA CAGACACAAA ATTGTGTCTC ACTGTACTCA CGTCGATTTT TTTAGCTACA        60

TTTGGGCATT ACGGTACTAA CAATATCAGA ACAATATTT TGAGTATCTT ACATAGATGA       120

AAACTTTCAT ATTTTTCATT TAAGTTTNGA TTCATTACTA TGGGTTAGAT GCCGTCGGGC       180

TNAGGTGCTG GAGCTCTCTT GTTCTCAATC TCTCCTTTTG TCCTTATTCA CCACAATGTT       240

AATTTGGAGC TGAGAGATTC ATCACTGACC GCATCTATTA CCTTTCTGCT TCACCTTGGC       300

TCGCTTTGGC AACTTCGCCT TTGGACTTCT AGCATGACAG ACATAGCTGC GCTTGGAGAT       360

CCTCAGAGGT AACTTTCTTG ATGGCTCAAA ATCNGAGTTC TTGTTTCATC TTCTGTTCTA       420

CTATGACTTA TACTTTCGTT AAN                                              443
```

(2) INFORMATION FOR SEQ ID NO: 12:

(i) SEQUENCE CHARACTERISTICS:
        (A) LENGTH: 319 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
CATAATTGTA CAGACACAAA ATTGTGCTCA CTGTACNCAC GTCGATTTTT TAGCTACAT         60

TTGGGCATTA CGGTACTAAC AATATCAGAA ACAATATTTT GAGTATCTTA CATAGATGAA       120

AACTTTCATA TTTTTCATTT AAGTTTGATT CATTACTATG GGTTAGATGC CGTCGGGCTA       180

GGGGCTGGAG CTCTCTTGTT CTCAATCTCT CCTTTTGTCC TTATTCACCA CAATGTTAAT       240

TTGGNGCTGA GAGATTCATC ACTGACCGCA TCTATTACCN TTCTGCTTCA NCTTGGCTGC       300
```

```
TTTGGNAACT TCGNCTTTG                                                      319

(2) INFORMATION FOR SEQ ID NO: 13:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

TCTATGAGAA AGAACCAGGA GAGGAGCTAC TCATTCCCTG TACGGTCTAT TTTAGTTTTC           60

TGATGGATTC TCGCAATGAG GTTTGGTGGA CCATTGATGG AAAAAAACCT GATGACATCA          120

CTATTGATGT CACCATTAAC GAAAGTATAA GTCATAGTAG AACAGAAGAT GAAACAAGAA          180

CTCAGATTTT GAGCATCAAG AAAGTTACCT CTGAGGATCT CAAGCGCANT ANTGTCTGTC          240

ATGCTAGAAG TGCCAAAGGC GAAGTTGCCA AAGCAGCCAA GGTGAAGCAG AAAGTGCCAG          300

CTCCAAGATA CACAGTGGAA CTGGCTTGTG GTTTTGGAGC CACAGTCCTG CTAGTGGTGA          360

TTCTCATTGT TGTTTACCAT GTTTACTTGG CTAGAG                                   396

(2) INFORMATION FOR SEQ ID NO: 14:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GCTCTCCAAA AAATGCAGTG CCCCCTGTGA TCCATTCACC TAATGATCAT GTGGTCTATG           60

AGAAAGAACC AGGAGAGGAG CTACTCATTC CCTGTACGGT CTATTTTAGT TTTCTGATGG         120

ATTCTCGCAA TGAGGTTTGG TGGACCATTG ATGGAAAAAA ACCTGATGAC ATCACTATTG         180

ATGTCACCAT TAACGAAAGT ATAAGTCATA GTAGAACAGA AGATGAAACA AGAACTCAGA         240

TTTTGAGGCA TCAAGAAAGT TACCTCTGAG GATCTCAAGC GCNTAATNGT CTGTNCATGG         300

CTAGGAAGTG CCAAAGNGGA AGTTGGCCAA AGGCAGCCAA GGTNGAGGCA GGAAAGGTTA         360

TTAGGTGGCG GTTCAGTTGA TGGATTCTCT TCAGGNTCCC AATTTTAACN TTGTTGGGTG         420

GATTTA                                                                   426

(2) INFORMATION FOR SEQ ID NO: 15:

(i) SEQUENCE CHARACTERISTICS:
        (A) LENGTH: 570 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

TTCGGCACAG GGAACCTCCA AACATATAGA AGTAAAGACA CAGGGCTGTT ATAAAATACA          60

GAATTTTAAT AATGTAATAC CCGAAGTATG AACTTGAGTT TCCTCATTGC CTTAATTTCA         120

AATAATGGAA ATTACACATG TGTTGTTACA TATCCAGAAA ATGGACGTAC GTTTCATCTC         180

ACCAGGACTC TGACTGTAAA GGTAGTAGGC TCTCCAAAAA ATGCAGTGCC CCTGTGATC          240
```

| | |
|---|---|
| CATTCACCTA ATGATCATGT GGTCTATGAG AAAGAACCAG GGAGAGTAGC TACTCATTCC | 300 |
| CTGTACGGTC TATTTTAGTT TTCTGATGGA TTCTCGCAAT GGAGGTTTNG TGGGACCATT | 360 |
| TGATGGGAAA AAAACCTGGA TNGACATCAN TATTTGATGT TCACCATTTA ACGGAAAGTA | 420 |
| TTAAGTCCTT AGTTAGGANC AGGTGGTTGA ANACAGGAAN TCCGGTTTTT GAGGCTTCAG | 480 |
| GAAAGTTTAC CCCTGNGGGT TCTTCAGGNG CCGATTGTTN TGTTCNTTGT TNGGAGGTGN | 540 |
| CCCAGNGGAA GTTTTGNCCA AGGCGGCCAG | 570 |

(2) INFORMATION FOR SEQ ID NO: 16:

(i) SEQUENCE CHARACTERISTICS:
        (A) LENGTH: 256 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

| | |
|---|---|
| TAGTACTATC AACATAGAAA NCATGTTTAT ACCATTTAAA ATCATAATTT AAATGATTTT | 60 |
| CATTTTAGCA ATTGTGGCTG CTGGTATATT ATAAACCTGC TTAAATATTG ATACATAGTG | 120 |
| TTTAANATAA TATTATAATT CTGCATTTTT GGAAAATAAA CATTCAATAC CTTAATTAGT | 180 |
| TGCATACAAT TGGATGGCTG CTATTAATAA NGTTTTACAA CTACAGATAA TGCTTCTAAT | 240 |
| ANTATTANCG GGNATA | 256 |

(2) INFORMATION FOR SEQ ID NO: 17:

(i) SEQUENCE CHARACTERISTICS:
        (A) LENGTH: 333 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

| | |
|---|---|
| GAACAGAAGA TGAAACAAGA ACTCAGATTT TGAGCATCAA GAAAGTTACC TCTGAGGATC | 60 |
| TCAAGCGCAN TATTGTCTGT CATGCTAGAA GTGCCAAAGG GAANGTTGCC AAAGCAGCCA | 120 |
| AGGTGAAGCA GAAAGGTAAT AGATGCGGTC AGTGATGAAT CTCTCAGCTC CAAATTAACA | 180 |
| TTGTGGGTGA ATAAGGACAA AAGGAGAGAT TGAGGAACAA GAGAGCTCCA GCACCTAGCC | 240 |
| TGACGGCATC TTAACCCCAT AGTAATTGAA TCCAACTTTA AATGGAAAAN TTTGNAGTTT | 300 |
| TTTCATCCTT NGGTAGGGTA CTTCAANTTT TGT | 333 |

(2) INFORMATION FOR SEQ ID NO: 18:

(i) SEQUENCE CHARACTERISTICS:
        (A) LENGTH: 271 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

| | |
|---|---|
| TTCTGACAAG AAGGCTTTAT AATTTCCATT TATTGTAGAA TAATATAGTA CTATCAACAT | 60 |
| AGAAATCATG TGTATACCAT TTAAAATCAT AATTTAAATG ATTTTCATTT TAGCAATTGT | 120 |
| GGCTGCTGGG ATATTATAAA CCTGCTTAAA TATTGATACA TAGNGTTTAA AATAATATTA | 180 |

TAATTATGCA NTTTTGGGGA AATAAACATT CAATACCCNT AATAGGTGCA TACAATTGGG    240

AGGGCTGCNA TTAATAATGG TTTCCACNAC C    271

(2) INFORMATION FOR SEQ ID NO: 19:

(i) SEQUENCE CHARACTERISTICS:
        (A) LENGTH: 214 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

TATTTTCCAA AAATGCATAA TTATAATATT ATTTYAMMCA CTATGTATCA ATATTTAAGC    60

AGGTTTATAA TATACCAGCA GCCACAATTG CTAAAATGAA ATCATTTAA ATTATGATTT    120

TAAATGGTAT ACACATGATT YCTATGTTGA TAGTACTATA TTATTCTACA ATAAATGGAA    180

ATTATAACGC CTTCTTGTCA GAAGTGCTGC TCCT    214

(2) INFORMATION FOR SEQ ID NO: 20:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GCTTTATAAT ATTTTANTTA TTGTAGAATA ATATAGTACT ATCAACATAG AAATCATGTG    60

TATACCATTT AAAATCATAA TTTAAATGAT TTTCATTTTA GCAATTGTGG CTGCTGGGTA    120

TATTATAAAC CTGCTTAAAT ATTGATACAT AGTGTTAAAA ATAATATTAT AATTATGGCA    180

TTTTTGGGAA ATAAACATTC AATACCTTAA TTGGNTGGCA TACAATGGGG TGGGCNGGCT    240

ATTAATAATG GTTTTACAAC TACAGGGTAA TGGCNTCCTA ATAATATTAA AGGGGGGNTA    300

TAATTCCCC    309

(2) INFORMATION FOR SEQ ID NO: 21:

(i) SEQUENCE CHARACTERISTICS:
        (A) LENGTH: 486 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

CCGGNTCCG CTTTGGCCAG ANGTNGGAAG GAAGCAGTGC CCGGCGACAC TCCACCCATC    60

CCGGCTGCTT TTGCTGCGCC CTCTCAGCTT CCCAAGAAAG GATGACACTT CTGTGGTGTG    120

TAGTGAGTCT CTACTTTTAT GGAATCCTGC AAAGTGATGC CTCAGGTAAG TGAATGGCTT    180

TTGACAATGT ATTAAAATGC AAGTCATGCG TAGGGTAATG AGTCCACTCT TCCTGAAAAT    240

GAATTTAAAT AAACATAATG TTATTCATGT CCATTGTCTT CTGCGGTANA ANATNAATCA    300

TAAAGCAGAA TAATAGAATT TTGATGATGG GAAAGAACCA TTGCTGTCTC TAGTCTTCAT    360

GGGGATAGGA GTACACAGGG GGCAGTGGGG CCGCTGTGTT TTAAACACAG GTATTTTTCC    420

NTACCTTCAC ATTCAGCCAA CTAGGATATT TGCTTTTTCC CTTACCTCAG TCCCTTGGGG    480

GAAAAT                                                                                  486

(2) INFORMATION FOR SEQ ID NO: 22:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

TAATGATCAT GTGGTCTATG AGAAAGAACC AGGANAGGAG CTACTCATTC CCTGTACGGT        60

TATTTTAGTT TTCTGATGGA TTCTCGCAAT GAGGTTTGGT GGACCATTGA TGGANAAAAA       120

CCTGATGACA TCACTATTNG ATTGTCAACA TTTAACNGA                              159

(2) INFORMATION FOR SEQ ID NO: 23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

GGATCCATGA CACTTCTGTG GTGTG                                              25

(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GTCGACTCAC TGACCGCATC T                                                  21

(2) INFORMATION FOR SEQ ID NO: 25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

GGATCCATCC GCCATCATGA CACTTCTGTG GTGTG                                   35

(2) INFORMATION FOR SEQ ID NO: 26:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

-continued

```
TCTAGAAAAG CGTAGTCTGG GACGTCGTAT GGGTACTGAC CGCATCT                   47

(2) INFORMATION FOR SEQ ID NO: 27:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

GACTGGATCC GCCATCATGA CACTTCTGTG GTGTG                                35

(2) INFORMATION FOR SEQ ID NO: 28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

GAATTCCTCA CTGACCGCAT CT                                              22

(2) INFORMATION FOR SEQ ID NO: 29:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 29:

GACTGGATCC GCCATCATGA CACTTCTGTG GTGTG                                35

(2) INFORMATION FOR SEQ ID NO: 30:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

GACTGGTACC CATAGAAATC ATGTGTATAC C                                    31
```